(12) United States Patent
Deng et al.

(10) Patent No.: US 10,758,405 B2
(45) Date of Patent: Sep. 1, 2020

(54) DUAL MODALITY ENERGY DELIVERY SYSTEM

(71) Applicant: Johnson & Johnson Consumer Inc., Skillman, NJ (US)

(72) Inventors: Austin Deng, Cherry Hill, NJ (US); Laura Higgins, Jersey City, NJ (US); Alexandru Paunescu, Clinton, NJ (US); Ryan Walsh, Downingtown, PA (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 113 days.

(21) Appl. No.: 16/117,386

(22) Filed: Aug. 30, 2018

(65) Prior Publication Data
US 2019/0070036 A1    Mar. 7, 2019

Related U.S. Application Data

(60) Provisional application No. 62/553,167, filed on Sep. 1, 2017.

(51) Int. Cl.
*A61F 7/02* (2006.01)
*A61F 7/10* (2006.01)
(Continued)

(52) U.S. Cl.
CPC .................. *A61F 7/02* (2013.01); *A61F 7/03* (2013.01); *A61F 7/10* (2013.01); *A61F 7/106* (2013.01);
(Continued)

(58) Field of Classification Search
CPC ..... A61F 7/02; A61F 7/03; A61F 7/08; A61N 5/06; A61N 5/0613; A61N 5/0616; A61N 5/0625
(Continued)

(56) References Cited

U.S. PATENT DOCUMENTS 7,125,416 B2   10/2006   Kent et al.
8,257,416 B2    9/2012   Vanderschuit
(Continued)

FOREIGN PATENT DOCUMENTS

KR     20140136590 A    12/2014
WO   WO2016203461 A1   12/2016

OTHER PUBLICATIONS

U.S. Appl. No. 62/553,167, filed Sep. 1, 2017, Johnson & Johnson Consumer Inc.
(Continued)

*Primary Examiner* — John P Lacyk

(57) ABSTRACT

An economical dual modality system can be manufactured and used in a method including the steps of assembling a system including a durable energy subsystem and a replaceable thermal subsystem, activating the replaceable thermal subsystem, attaching the system to a desired treatment area of a user's body, and activating the durable energy subsystem. The durable energy subsystem is arranged and configured to deliver energy, and the replaceable thermal subsystem is arranged and configured to be coupled to the durable energy subsystem arranged and configured to deliver thermal energy. The replaceable thermal subsystem delivers thermal energy to the desired treatment area at a predetermined temperature range for at least 30 minutes, and the durable energy subsystem delivers energy from the group consisting of non-visible light electromagnetic radiation, visible light radiation, electromagnetic field, microcurrent, electrical stimulation, iontophoresis, sonophoresis and combinations thereof independently of the thermal energy.

14 Claims, 18 Drawing Sheets

(51) Int. Cl.
*A61N 5/06* (2006.01)
*A61F 7/03* (2006.01)
*A61M 37/00* (2006.01)
*A61N 2/00* (2006.01)
*A61N 2/02* (2006.01)
*A61H 23/00* (2006.01)
*A61N 7/00* (2006.01)
*A61F 7/00* (2006.01)
*A61N 1/32* (2006.01)
*A61N 1/36* (2006.01)
*A61N 1/30* (2006.01)

(52) U.S. Cl.
CPC ......... *A61H 23/00* (2013.01); *A61M 37/0092* (2013.01); *A61N 2/002* (2013.01); *A61N 2/02* (2013.01); *A61N 5/06* (2013.01); *A61N 5/0613* (2013.01); *A61N 5/0616* (2013.01); *A61N 5/0625* (2013.01); *A61N 7/00* (2013.01); *A61F 2007/0052* (2013.01); *A61F 2007/0078* (2013.01); *A61F 2007/0086* (2013.01); *A61F 2007/0095* (2013.01); *A61F 2007/0225* (2013.01); *A61F 2007/0226* (2013.01); *A61F 2007/0285* (2013.01); *A61F 2007/0292* (2013.01); *A61H 2201/10* (2013.01); *A61M 2205/05* (2013.01); *A61N 1/30* (2013.01); *A61N 1/325* (2013.01); *A61N 1/36021* (2013.01); *A61N 2005/0645* (2013.01); *A61N 2005/0651* (2013.01); *A61N 2005/0659* (2013.01); *A61N 2005/0662* (2013.01)

(58) Field of Classification Search
USPC ..................................................... 600/13–14
See application file for complete search history.

(56) References Cited

U.S. PATENT DOCUMENTS

| | | |
|---|---|---|
| 8,858,607 B1 | 10/2014 | Jones |
| 9,370,449 B2 | 6/2016 | Anderson et al. |
| 2006/0235494 A1 | 10/2006 | Vanderschuit |
| 2007/0016271 A1 | 1/2007 | Hammond |
| 2010/0089381 A1* | 4/2010 | Bolmer .................. F28D 20/02 126/263.01 |
| 2012/0004711 A1 | 1/2012 | Hilty |
| 2012/0016174 A1 | 1/2012 | De Taboada et al. |
| 2012/0035689 A1 | 2/2012 | Turtzo |
| 2013/0066404 A1 | 3/2013 | Tapper et al. |
| 2013/0274836 A1 | 10/2013 | Downs |
| 2014/0074010 A1 | 3/2014 | Veres et al. |
| 2014/0206947 A1 | 7/2014 | Isserow |
| 2015/0165231 A1* | 6/2015 | Scheja ..................... A61F 7/02 604/20 |
| 2015/0265780 A1 | 9/2015 | Pesach et al. |
| 2015/0290470 A1 | 10/2015 | Tapper et al. |
| 2017/0014264 A1 | 1/2017 | Bradley et al. |

OTHER PUBLICATIONS

U.S. Appl. No. 16/117,300, filed Aug. 30, 2018, Johnson & Johnson Consumer Inc.
U.S. Appl. No. 16/117,342, filed Aug. 30, 2018, Johnson & Johnson Consumer Inc.
U.S. Appl. No. 16/117,370, filed Aug. 30, 2018, Johnson & Johnson Consumer Inc.
International Search Report, Application No. PCT/IB2018/056679, dated Jan. 31, 2019.

* cited by examiner

DUAL MODALITY ENERGY DELIVERY SYSTEM

CROSS-REFERENCE TO RELATED APPLICATIONS

This application claims the benefit of U.S. provisional application 62/553,167 filed on Sep. 1, 2017.

FIELD OF THE INVENTION

The present invention generally relates to a system which utilizes light therapy in the treatment of musculoskeletal pain, reduction of edema and inflammation, and promoting the healing of tissues, especially soft tissues like muscle, tendons, and ligaments. More specifically, the invention relates to a system with a durable energy subsystem, a replaceable thermal subsystem, and a means to couple the durable energy subsystem and the replaceable thermal subsystem to a desired treatment area of a user's body.

BACKGROUND OF THE INVENTION

Light, when delivered to the body, has been shown to elicit a wide range of therapeutic effects. Specifically, light can be used as a therapeutic agent for various disorders. For example, light therapy devices have been used for treatment of musculoskeletal pain.

Examples of light emitters used in light therapy may include lasers and light emitting diodes (LEDs). LEDs are often preferred for having the ability to illuminate a larger area than a laser. Light emitted from LEDs may decrease wrinkles and skin roughness by increasing collagen and elastin synthesis, and reduce pigmentation in human skin. Furthermore, the emitted light may protect against subsequent photo damage, prevent post-inflammatory hyperpigmentation and reduce scar formation during healing. Also, the illumination from blue, red, or infrared LEDs may cause generation and release of nitric oxide, which may subsequently lead to pain relief.

Light therapy is often delivered in a doctor's office in light chambers that deliver light to the entire body surface. The amount of light delivered is based on the amount of time the patient is exposed to light and the intensity of the light. The light is delivered to the entire body even though the region that requires treatment often composes a fraction of the overall surface area of the body. When receiving this modality of light therapy, the patient must wear protective eyewear to prevent exposure of light to the eyes. If the patient is exposed to more light than intended, cellular damage and/or burns may occur over a large portion of the body, leading to significant discomfort and even medical treatment. So typically, a trained professional is required to deliver the light to ensure that the patient receives the correct dose of light and that sensitive areas, such as the eyes, are not exposed to the light.

For home use, focused light devices have been developed. Focused light solves the issue of light exposure to areas that do not need therapy because the user directs the light to the area where the therapy is needed. A disadvantage of some known therapeutic device is that it is inconvenient for the user to hold the device in position for an extended period of time. This is particularly true if the area to be treated is difficult to reach, such as the user's back or feet. In this regard, it would be desirable to provide a device that would be more conveniently held in position for an extended period of time without requiring the user to hold it.

Typically, the light therapy device includes a rigid housing having an applicator end. The applicator end is integrally attached to the housing thus forming a self-contained unit. Light emitting diodes ("LEDs") are positioned in the housing such that they emit light from the applicator end of the device. The housing generally also contains a battery pack and a processor for controlling the frequency and duration of light delivery. Other electrical components may be provided in the housing depending on the electronic features of the device.

To operate the known therapeutic device, a user grasps the rigid housing of the device and positions the applicator end of the device on the area to be treated. The LEDs are then energized causing light radiation at the applicator end of the device. For effective treatment, the radiation must be applied for a specified time period. This requires the device to be held in place by the user. Depending on the area and problem that is treated, the duration of the treatment can vary from a few minutes to several hours.

A further disadvantage of the known devices is that, depending on the area treated, once the device is strapped, a user can no longer see the control display. For example, if the user straps the unit to his back, he can no longer see the face of the housing and will be unable to monitor the display. Furthermore, to change a setting, the user will be required to unstrap the device to access the control panel, and then re-strap the unit once the setting has been changed. It would be desirable, to provide a unit that could comfortably be applied to the area for treatment while allowing the user convenient access to the control panel.

The application of thermal energy (heat or cold) is also known as therapies to treat aches, bruises, pains, sprains, and strains. The combination of light and thermal energy is also desired for the treatment of pain and promoting the healing of tissues. Devices that combine both forms of energy may be able to bring greater relief to the user. Portable devices that deliver both light and thermal energy have issues with the required power to run both energy sources. Bulky batteries, or the need to plug into an electric outlet, hinder the convenience desired in a combination device. So, a device with a durable light emitter and a replaceable thermal energy source is desirable.

Cold and heat packs, such as gel-based packs, are widely used for first aid. Cold packs may be used to reduce swelling or to help recover from the sun. The gel inside the gel packs is provided to store cold/warmth such that a target area can be slowly cooled or heated during therapy. Typically, the gel packs are provided with a flexible package material such that the pack may be formed and applied to uneven target treatment areas such as limbs, faces, joints, etc. Often, the gel packs are reusable, and may be reheated in, for example a microwave oven, or re-cooled in a freezer. A disadvantage of these is the user may apply an overheated or overcooled gel-pack to the site of pain, potentially causing more harm to the site of pain.

In summary, there is a need for improved wearable devices delivering phototherapy and thermal therapy that are comfortable, easy to operate and allow for relief from musculoskeletal pain and other ailments (including injury to bones, joints, muscles, tendons, ligaments, or nerves) without requiring long treatment durations or a visit to a physician's office.

SUMMARY OF THE INVENTION

Surprisingly, we have found that an economical dual modality system can be manufactured and used in a method including the steps of assembling a system including a durable energy subsystem and a replaceable thermal subsystem, activating the replaceable thermal subsystem, attaching the system to a desired treatment area of a user's body, and activating the durable energy subsystem. The durable energy subsystem is arranged and configured to deliver energy, and the replaceable thermal subsystem is arranged and configured to be coupled to the durable energy subsystem arranged and configured to deliver thermal energy. The replaceable thermal subsystem delivers thermal energy to the desired treatment area at a predetermined temperature range for at least 30 minutes, and the durable energy subsystem delivers energy from the group consisting of non-visible light electromagnetic radiation, visible light radiation, electromagnetic field, microcurrent, electrical stimulation, iontophoresis, sonophoresis and combinations thereof independently of the thermal energy.

DETAILED DESCRIPTION OF THE INVENTION

The present invention relates to a system to provide superior treatment to an area of a user's body. The following description is presented to enable one of ordinary skill in the art to make and use the invention. Various modifications to the embodiments and the generic principles and features described herein will be readily apparent to those skilled in the art. Thus, the present invention is not intended to be limited to the embodiments shown, but is to be accorded the widest scope consistent with the features described herein.

The dual modality system described herein uses a durable energy subsystem, a replaceable thermal subsystem, and a means to couple the durable energy subsystem and the replaceable thermal subsystem to a desired treatment area of a user's body. The energy from the dual modality system may be delivered continuously or discontinuously, or delivered intermittently (also called "pulsed").

As used herein the specification and the claims, the term "topical" and variants thereof mean of or applied to an isolated part of the body. This includes, without limitation skin, mucosa, and enamel.

The method for applying a desired treatment to an area of a user's body uses the herein system where the dual modality system is coupled to the desired treatment area of a user's body, and a treatment cycle is initiated.

Figure 1:
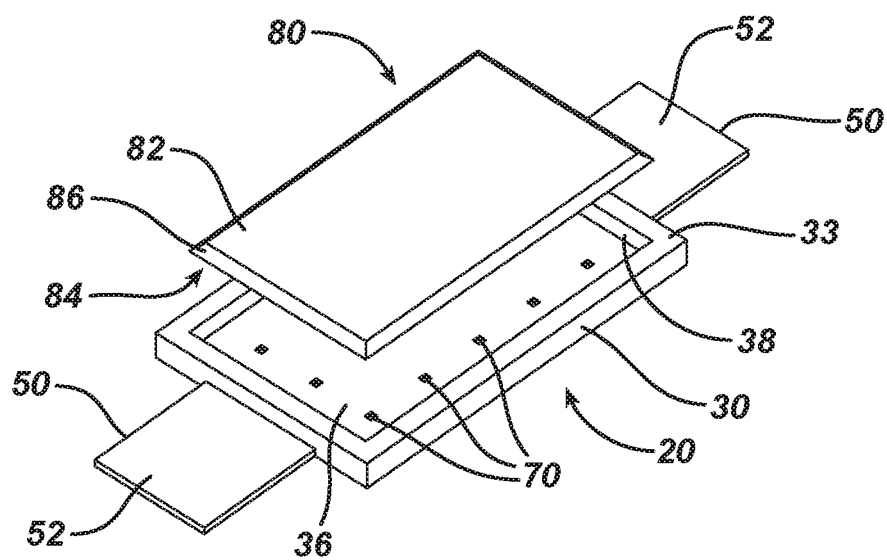
FIG. 1 is an exploded view of an embodiment of a dual modality system of the present invention.

FIGS. 1 to 4 show a first embodiment of a dual modality system 10 of the present invention. FIG. 1 is an exploded view of dual modality system 10 which has a durable energy subsystem chassis 20 and a replaceable thermal subsystem 80.

Replaceable thermal subsystem 80 has a first surface 82, a second surface 84, and four side surfaces 86. In some embodiments, replaceable thermal subsystem 80 includes a heat source, while in other embodiments, replaceable thermal subsystem 80 includes a cooling source.

Durable energy subsystem chassis 20 has a main body 30 and end tabs 50. Main body 30 has a first longitudinal end 31, a second longitudinal end 32, a first surface 33, a second surface 34, and a receptacle defined by bottom surface 36 and inner side surfaces 38. Disposed in or proximate to second surface 34 of main body 30 are a plurality of energy emitters 70. End tabs 50 are preferably flexible and are disposed on first longitudinal end 31 and second longitudinal end 32. End tabs 50 each has a first surface 52, and a second surface 54. In some embodiments, durable energy subsystem chassis 20 is flexible. Durable energy subsystem chassis 20 may optionally include at least one component arranged and configured to communicate data through wired or wireless communication with external devices, such as a smart phone or other computer or communication device connected to a network.

Figure 2:
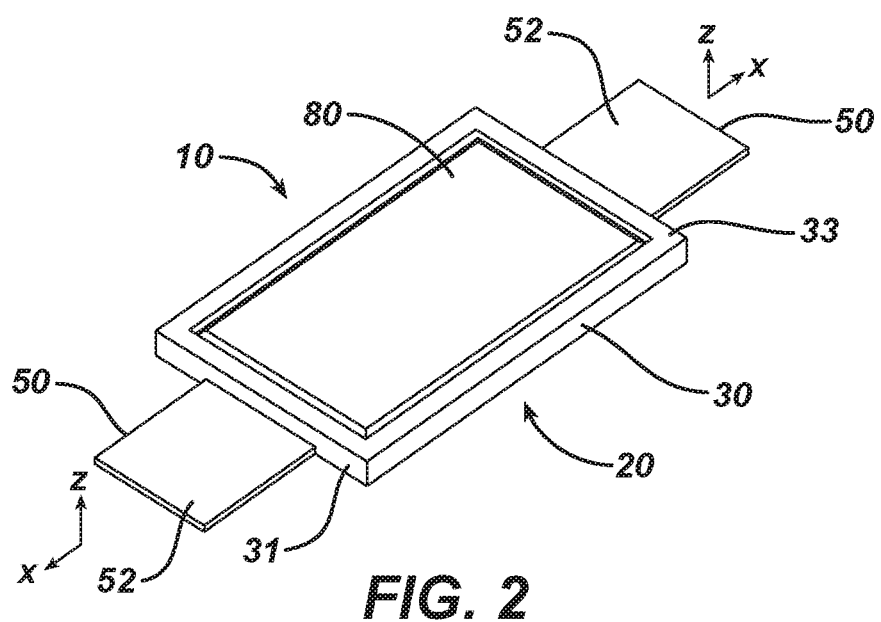
FIG. 2 is a top perspective view of the dual modality system embodiment of FIG. 1.
Figure 3:
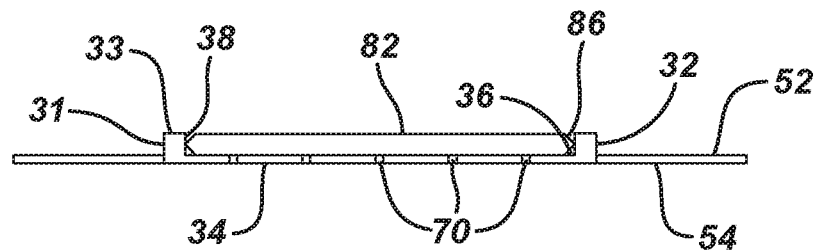
FIG. 3 is a cross-sectional view of the of the embodiment of FIG. 2 in the x-z plane.
Figure 4:
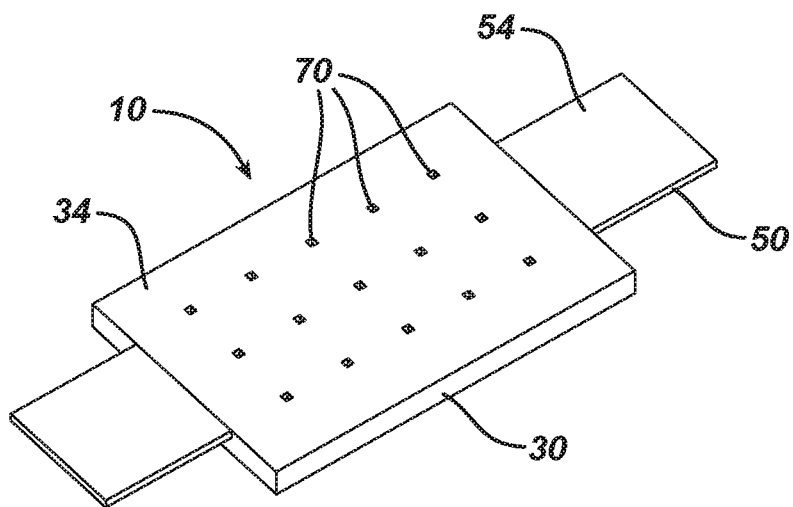
FIG. 4 is a bottom perspective view of the embodiment of FIG. 1.

Replaceable thermal subsystem 80 is coupled to the durable energy subsystem chassis 20 and arranged and configured to deliver thermal energy. FIGS. 2 and 4 are top and bottom, respectively, perspective views of dual modality system 10 when the system is assembled. FIG. 3 is a cross-sectional view of dual modality system 10 in the x-z plane of FIG. 2. When assembled, replaceable thermal subsystem 80 is disposed in receptacle of main body 30 of durable energy subsystem chassis 20 so that second surface 84 of replaceable thermal subsystem 80 at least partially contacts receptacle bottom surface 36, and side surfaces 86 of subsystem 80 at least partially contact receptacle inner side surfaces 38. In some embodiments, replaceable thermal subsystem 80 is held in receptacle of main body 30 of durable energy subsystem chassis 20 by a friction fit between side surfaces 86 of subsystem 80 and receptacle inner side surfaces 38. In other embodiments, an adhesive may be used to hold replaceable thermal subsystem 80 in receptacle of main body 30. The adhesive may be located on any or all of second surface 84 or side surfaces 86 of replaceable thermal subsystem 80, or receptacle bottom surface 36 or inner side surfaces 38. In still other embodiments, durable energy subsystem chassis 20 may be held in receptacle of main body 30 via snap fit, pins, dowels, or other known coupling features in receptacle.

In this embodiment, replaceable thermal subsystem 80 is in the shape of a rectangular prism, and the receptacle of main body 30 is shaped to fit a rectangular prism.

As mentioned, end tabs 50 are disposed on first longitudinal end 31 and second longitudinal end 32. End tabs 50 may be integral to, or attached to, main body 30 of durable energy subsystem chassis 20. Attachment may be achieved using an adhesive or welding the end tabs 50 to main body 30. In addition, although energy emitters 70 are shown as disposed in or proximate to second surface 34 of main body 30, energy emitters 70 may be disposed on the surface of second surface 34 of main body 30. The plurality of energy emitters 70 are disposed in an emission region of the chassis having a length and a width, wherein the emission region length and emission region width are both substantially greater than an emission region depth. Although FIG. 4 shows fifteen energy emitters 70, the number of energy emitters 70 in energy subsystem chassis 20 will depend on the treatment type, intensity, and area being treated. The number of energy emitters 70 could be 1, or 2, or 5, or 10, or 20, or 50, or 100 or more.

Although FIG. 1 shows a regular array of energy emitters 70, the arrangement of these need not be a regular array. For example, one may desire to concentrate active elements in certain portions of energy subsystem chassis 20 and reduce the frequency/density of energy emitters 70 in other portions of energy subsystem chassis 20. In addition, energy emitters 70 may be placed around the periphery of energy subsystem chassis 20 and be coupled a wave guide that evenly distributes the energy throughout the chassis.

Possible cross-sectional shapes of energy emitters 70 include, but are not limited to, squares, rectangles, triangles, circles, ovals, kidneys, stars, crosses, characters, etc.

In use, durable energy subsystem chassis 20 and the replaceable thermal subsystem 80 comprising dual modality system 10 are coupled to a desired treatment area of a user's body. In this embodiment, adhesive disposed on second surface 54 of end tabs 50 acts as a means to couple dual modality system 10 to a desired treatment area of a user's body. In use, second surface 34 of main body 30 contacts the desired treatment area of a user's body.

In other embodiments, adhesive may also be disposed on second surface 34 of main body 30. In still other embodiments, end tabs 50 may not be present, and adhesive disposed on second surface 34 of main body 30 may act as a means to couple dual modality system 10 to the desired treatment area of a user's body.

Optionally, first embodiment dual modality system 10 also has release paper disposed on the regions having adhesive. In use, the user would first dispose replaceable thermal subsystem 80 into receptacle of main body 30, remove any release paper covering regions having adhesive, and place the dual modality system 10 on the desired treatment area of a user's body. In this embodiment, replaceable thermal subsystem 80 is integrated with the means to couple durable energy subsystem chassis 20 and replaceable thermal subsystem 80 to a desired treatment area of a user's body. Operational details of durable energy subsystem chassis 20 will be discussed later in this document.

Though shown as rectangular in shape, dual modality system 10 may have various sizes and shapes depending on the location of use for system. Possible shapes of the footprint left by dual modality system 10 include, but are not limited to, squares, rectangles, triangles, circles, ovals, kidneys, stars, crosses, characters, etc. The corners of such shapes, if any, may be angular or curved to reduce potential lift/removal points. The area of the treatment could be greater than about 1,000 cm$^2$, about 1,000 cm$^2$, or about 100 cm$^2$, or about 10 cm$^2$, or about 1 cm$^2$, or less than 1 cm$^2$.

Figure 5:
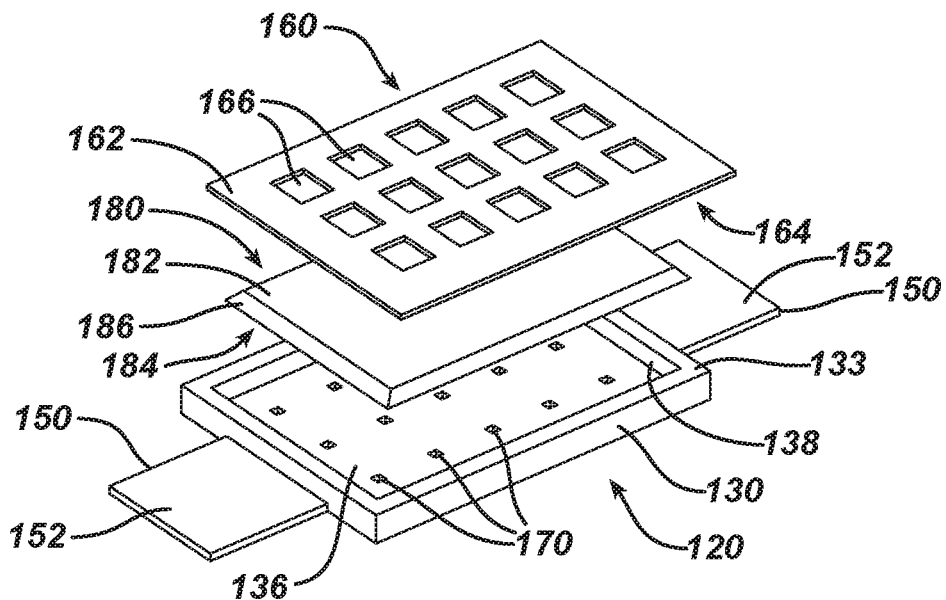
FIG. 5 is an exploded view of a second embodiment of a dual modality system of the present invention.

FIGS. 5 to 8 show a second embodiment of a dual modality system 100 of the present invention. FIG. 5 is an exploded view of dual modality system 100 which has a durable energy subsystem chassis 120, a replaceable thermal subsystem 180, and a cover 160. Replaceable thermal subsystem 180 has a first surface 182, a second surface 184, and four side surfaces 186, and may be a heat source or a cooling source.

Durable energy subsystem chassis 120 has a main body 130 and end tabs 150. Main body 130 has a first longitudinal end 131, a second longitudinal end 132, a first surface 133, a second surface 134, and a receptacle defined by bottom surface 136 and inner side surfaces 138. Disposed in or proximate to second surface 134 of main body 130 are a plurality of energy emitters 170. End tabs 150 are preferably flexible and are disposed on first longitudinal end 131 and second longitudinal end 132. End tabs 150 each have a first surface 152, and a second surface 154. In some embodiments, durable energy subsystem chassis 120 is flexible. Durable energy subsystem chassis 120 may optionally include at least one component arranged and configured to communicate data through wired or wireless communication with external devices, such as a smart phone or other computer or communication device connected to a network.

Cover 160 has a first surface 162, a second surface 164, and a plurality of apertures 166. Though cover 160 is shown as separate of energy subsystem chassis 120, in some embodiments it may be attached to main body 130 with pins or screws so that it may pivot between an open and shut position with respect to the receptacle of main body 130. In some embodiments, cover 160 may be attached to main body 130 via a living hinge (a thin flexure bearing hinge) made from the same material as the two pieces it connects. Also, though this embodiment shows cover 160 with a plurality of apertures 166, other embodiments may have covers with no apertures. The plurality of apertures 166 may provide air permeability or skin breathability to dual modality system 100.

Figure 6:
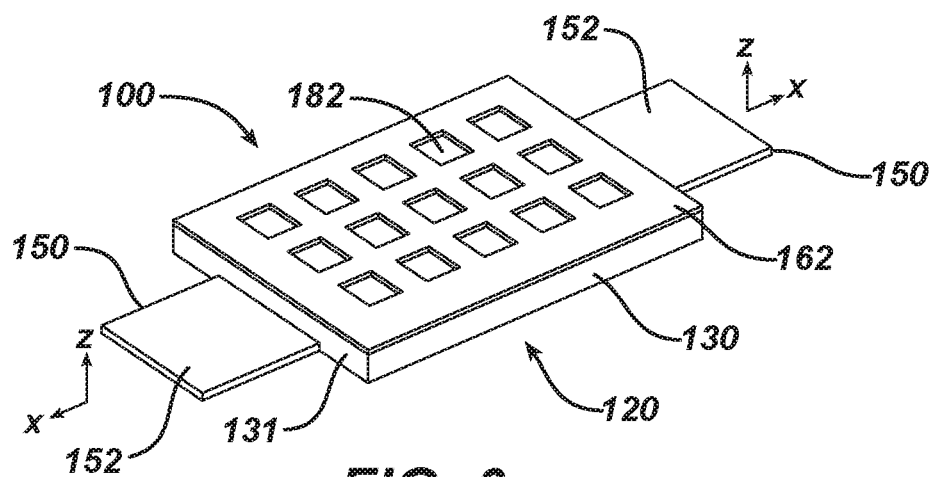
FIG. 6 is a top perspective view of the dual modality system embodiment of FIG. 5.
Figure 7:
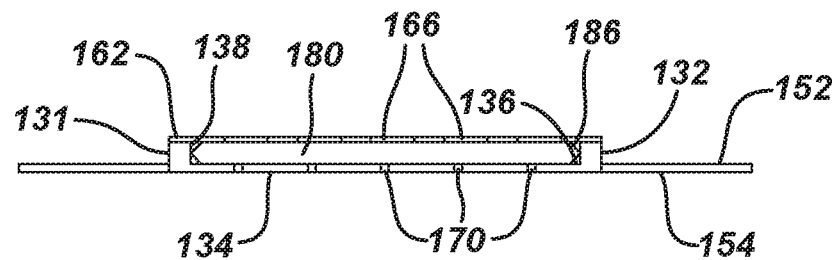
FIG. 7 is a cross-sectional view of the of the embodiment of FIG. 6 in the x-z plane.
Figure 8:
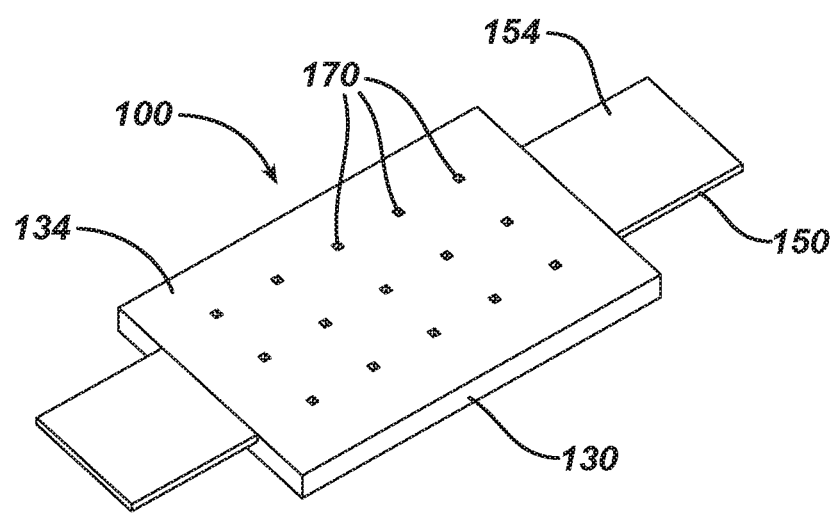
FIG. 8 is a bottom perspective view of the embodiment of FIG. 5.

Replaceable thermal subsystem 180 is coupled to the durable energy subsystem chassis 120 and arranged and configured to deliver thermal energy. FIGS. 6 and 8 are top and bottom, respectively, perspective views of dual modality system 100 when the system is assembled. FIG. 7 is a cross-sectional view of dual modality system 100 in the x-z plane of FIG. 6. When assembled, replaceable thermal subsystem 180 is disposed in receptacle of main body 130 of durable energy subsystem chassis 120 so that first surface 182 of replaceable thermal subsystem 180 may at least partially contacts second surface 164 of cover 160, second surface 184 of replaceable thermal subsystem 180 may at least partially contacts receptacle bottom surface 136, and side surfaces 186 of subsystem 180 may at least partially contact receptacle inner side surfaces 138.

In this embodiment, replaceable thermal subsystem 180 is held in receptacle of main body 130 of durable energy subsystem chassis 120 by cover 160. Cover 160 may be held in a closed position by a snap fit or other known means, and couples replaceable thermal subsystem 180 in the receptacle of main body 130. In other embodiments, an adhesive may be used to supplement cover 160. Since replaceable thermal subsystem 180 is held in receptacle of main body 130 by cover 160, replaceable thermal subsystem 180 may be smaller in volume that the volume of the receptacle of main body 130.

In this embodiment, replaceable thermal subsystem 180 is in the shape of a rectangular prism. In other embodiments, replaceable thermal subsystem 180 may be in other three-dimensional shapes.

End tabs 150, disposed on first longitudinal end 131 and second longitudinal end 132 of main body 130, may be integral to, or attached to main body 130 of durable energy subsystem chassis 120. Attachment may be achieved using an adhesive, or welding the end tabs 150 to main body 130 if they are not formed as integral to main body 130 of durable energy subsystem chassis 120. In addition, although energy emitters 170 are shown as disposed in or proximate to second surface 134 of main body 130, energy emitters 170 may be disposed on the surface of second surface 134 of main body 130. The plurality of energy emitters 170 are disposed in an emission region of the chassis having a length and a width, wherein the emission region length and emission region width are both substantially greater than an emission region depth.

Although FIG. 8 shows fifteen energy emitters 170 in a regular array, the number and arrangement of energy emitters 170 in energy subsystem chassis 120 will depend on the treatment type, intensity, and area being treated.

In use, durable energy subsystem chassis 120 and the replaceable thermal subsystem 180 comprising dual modality system 100 are coupled to a desired treatment area of a user's body. In this embodiment, adhesive disposed on second surface 154 of end tabs 150 acts as a means to couple dual modality system 100 to a desired treatment area of a user's body. In use, second surface 134 of main body 130 contacts the desired treatment area of a user's body.

In other embodiments, adhesive may also be disposed on second surface 134 of main body 130. In still other embodiments, end tabs 150 may not be present, and adhesive disposed on second surface 134 of main body 130 may act as a means to couple dual modality system 100 to the desired treatment area of a user's body.

Though not shown, second embodiment dual modality system 100 may also have release paper disposed on the regions having adhesive. In use, the user would first dispose replaceable thermal subsystem 180 into receptacle of main body 130, attach cover 160 to main body 130, remove any release paper covering regions having adhesive, and place the dual modality system 100 on the desired treatment area of a user's body. In this embodiment, replaceable thermal subsystem 180 is integrated with the means to couple durable energy subsystem chassis 120 and replaceable thermal subsystem 180 to a desired treatment area of a user's body. Operational details of durable energy subsystem chassis 120 will be discussed later in this document.

As discussed previously, dual modality system 100 may have various sizes and shapes depending on the location of use for system.

Figure 9:
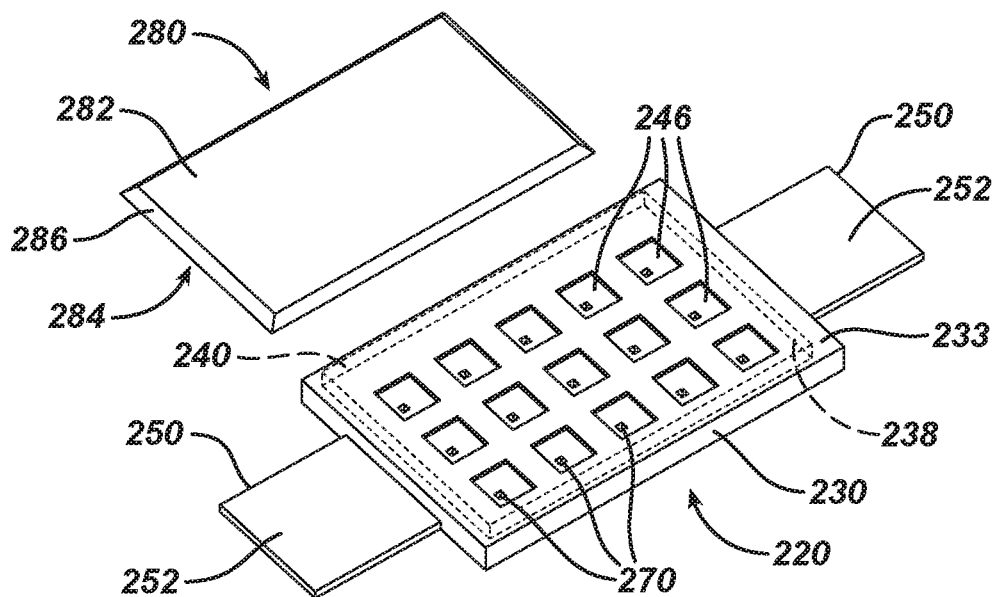
FIG. 9 is an exploded view of a third embodiment of a dual modality system of the present invention.

FIGS. 9 to 12 show a third embodiment of a dual modality system 200 of the present invention. FIG. 9 is an exploded view of dual modality system 200 which has a durable energy subsystem chassis 220 and a replaceable thermal subsystem 280. Replaceable thermal subsystem 280 has a first surface 282, a second surface 284, and four side surfaces 286, and may be a heat source or a cooling source.

Durable energy subsystem chassis 220 has a main body 230 and end tabs 250. Main body 230 has a first longitudinal end 231, a second longitudinal end 232, a first surface 233, a second surface 234, a plurality of apertures 246, and a receptacle defined by bottom surface 236, top surface 244, and three inner side surfaces 238. Slot 240 replaces the fourth inner side surface. Disposed in or proximate to second surface 234 of main body 230 are a plurality of energy emitters 270. End tabs 250 are preferably flexible and are disposed on first longitudinal end 231 and second longitudinal end 232. End tabs 250 each have a first surface 252, and a second surface 254. In some embodiments, durable energy subsystem chassis 220 is flexible. Durable energy subsystem chassis 220 may optionally include at least one component arranged and configured to communicate data through wired or wireless communication with external devices, such as a smart phone or other computer or communication device connected to a network.

Figure 10:
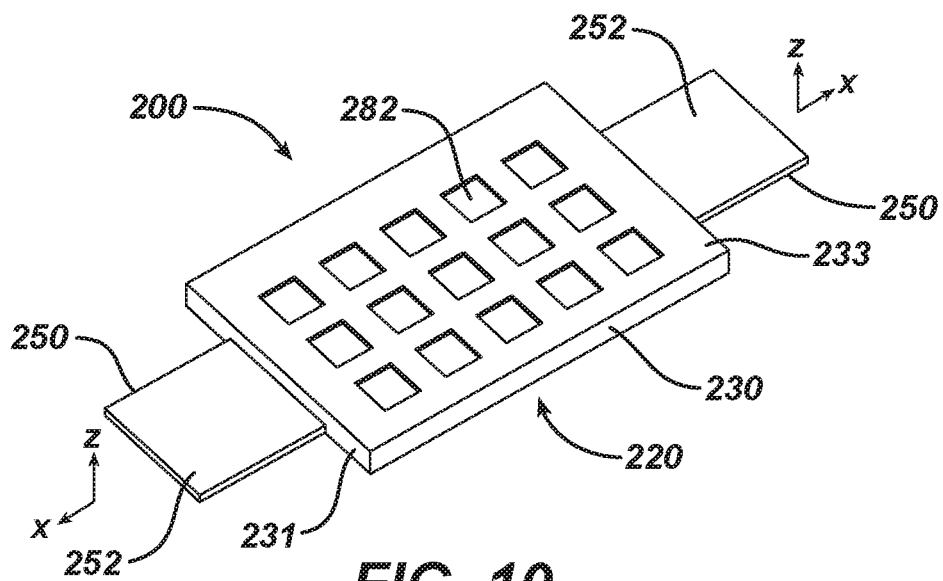
FIG. 10 is a top perspective view of the dual modality system embodiment of FIG. 9.
Figure 11:
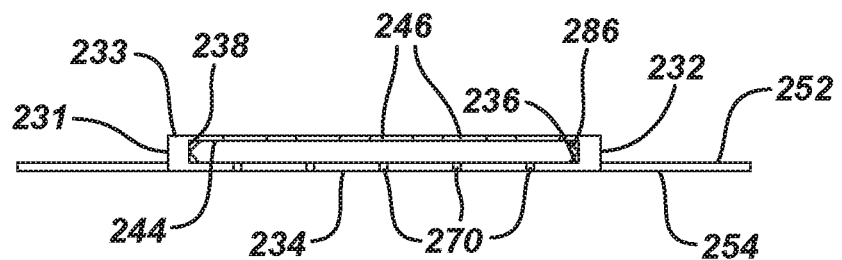
FIG. 11 is a cross-sectional view of the of the embodiment of FIG. 10 in the x-z plane.
Figure 12:
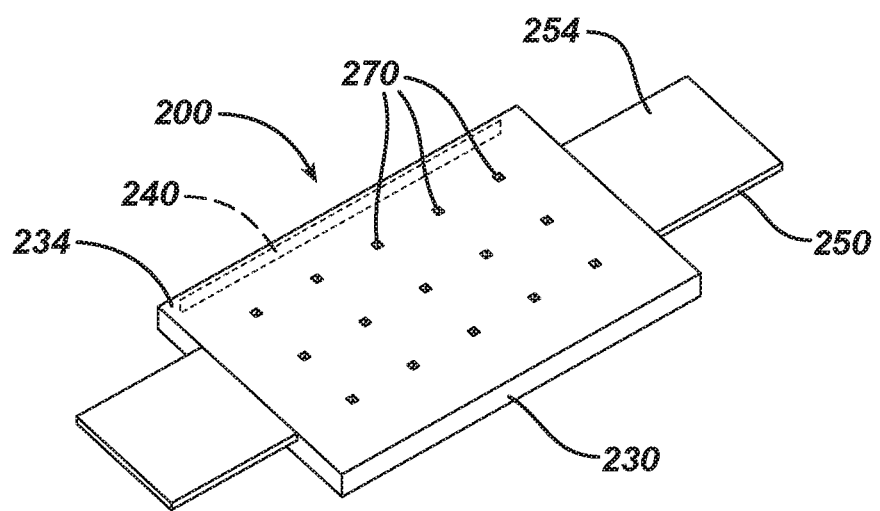
FIG. 12 is a bottom perspective view of the embodiment of FIG. 9.

Replaceable thermal subsystem 280 is coupled to the durable energy subsystem chassis 220 and arranged and configured to deliver thermal energy. FIGS. 10 and 12 are top and bottom, respectively, perspective views of dual modality system 200 when the system is assembled. FIG. 11 is a cross-sectional view of dual modality system 200 in the x-z plane of FIG. 10. When assembled, replaceable thermal subsystem 280 is disposed in the receptacle of main body 230 of durable energy subsystem chassis 220 so that first surface 282 of replaceable thermal subsystem 280 may at least partially contact receptacle top surface 244, second surface 284 of replaceable thermal subsystem 280 may at least partially contact receptacle bottom surface 236, and three side surfaces 286 of subsystem 280 may at least partially contact three inner side surfaces 238.

Replaceable thermal subsystem 280 is held in receptacle of main body 230 of durable energy subsystem chassis 220 by any number of friction fits. These include friction fits between side surfaces 286 and receptacle inner side surfaces 238, between first surface 282 and top surface 244, or between second surface 284 and receptacle bottom surface 236. In some embodiments, an adhesive or other coupling feature may be used to hold replaceable thermal subsystem 280 in receptacle of main body 230.

In this embodiment, replaceable thermal subsystem 280 is in the shape of a rectangular prism. In other embodiments, replaceable thermal subsystem 280 may be in other three-dimensional shapes.

End tabs 250, disposed on first longitudinal end 231 and second longitudinal end 232 of main body 230, may be integral to, or attached to main body 230 of durable energy subsystem chassis 220. Attachment may be achieved using an adhesive, or welding the end tabs 250 to main body 230 if they are not formed as integral to main body 230 of durable energy subsystem chassis 220.

In addition, though energy emitters 270 are shown as disposed in or proximate to second surface 234 of main body 230, energy emitters 270 may be disposed on the surface of second surface 234 of main body 230. The number, shape and arrangement of energy emitters 270 in energy subsystem chassis 220 will depend on the treatment type, intensity, and area being treated. The plurality of energy emitters 270 are disposed in an emission region of the chassis 220 having a length and a width, wherein the emission region length and emission region width are both substantially greater than an emission region depth.

In use, durable energy subsystem chassis 220 and the replaceable thermal subsystem 280 comprising dual modality system 200 are coupled to a desired treatment area of a user's body. In this embodiment, adhesive disposed on second surface 254 of end tabs 250 acts as a means to couple dual modality system 200 to a desired treatment area of a user's body. In use, second surface 234 of main body 230 contacts the desired treatment area of a user's body.

In other embodiments, adhesive may also be disposed on second surface 234 of main body 230. In still other embodiments, end tabs 250 may not be present, and adhesive disposed on second surface 234 of main body 230 may act as a means to couple dual modality system 200 to the desired treatment area of a user's body.

The plurality of apertures 246 disposed on main body 230 may provide air permeability or breathability to dual modality system 200. In some embodiments, main body 230 does not have apertures. In other embodiments, improved skin breathability may be achieved by main body 230 having a discontinuous skin-contact surface.

Though not shown, third embodiment dual modality system 200 may have release paper disposed on the regions having adhesive. In use, the user would first dispose replaceable thermal subsystem 280 into receptacle of main body 230 by sliding the subsystem through slot 240, remove any release paper covering regions having adhesive, and place the dual modality system 200 on the desired treatment area of a user's body. In this embodiment, replaceable thermal subsystem 280 is integrated with the means to couple durable energy subsystem chassis 220 and replaceable thermal subsystem 280 to a desired treatment area of a user's body. Operational details of durable energy subsystem chassis 220 will be discussed later in this document.

As discussed previously, dual modality system 200 may have various sizes and shapes depending on the location of use for system.

Figure 13:
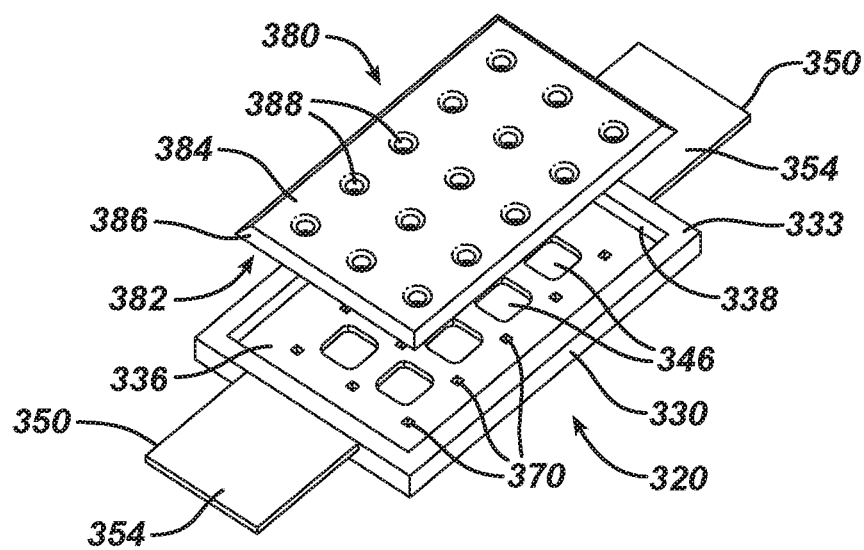
FIG. 13 is an exploded view of a fourth embodiment of a dual modality system of the present invention.

FIGS. 13 to 16 show a fourth embodiment of a dual modality system 300 of the present invention. FIG. 13 is an exploded view of dual modality system 300 which has a durable energy subsystem chassis 320 and a replaceable thermal subsystem 380. Replaceable thermal subsystem 380 has a first surface 382, a second surface 384, four side surfaces 386 and apertures 388, and may be a heat source or a cooling source.

Durable energy subsystem chassis 320 has a main body 330 and end tabs 350. Main body 330 has a first longitudinal end 331, a second longitudinal end 332, a first surface 333, a second surface 334, a plurality of apertures 346, and a receptacle defined by bottom surface 336 and four inner side surfaces 338. Disposed in first surface 333 of main body 330 are a plurality of energy emitters 370. End tabs 350 are preferably flexible and are disposed on first longitudinal end 331 and second longitudinal end 332. End tabs 350 each have a first surface 352, and a second surface 354. In some embodiments, durable energy subsystem chassis 320 is flexible. Durable energy subsystem chassis 320 may optionally include at least one component arranged and configured to communicate data through wired or wireless communication with external devices, such as a smart phone or other computer or communication device connected to a network.

Figure 14:
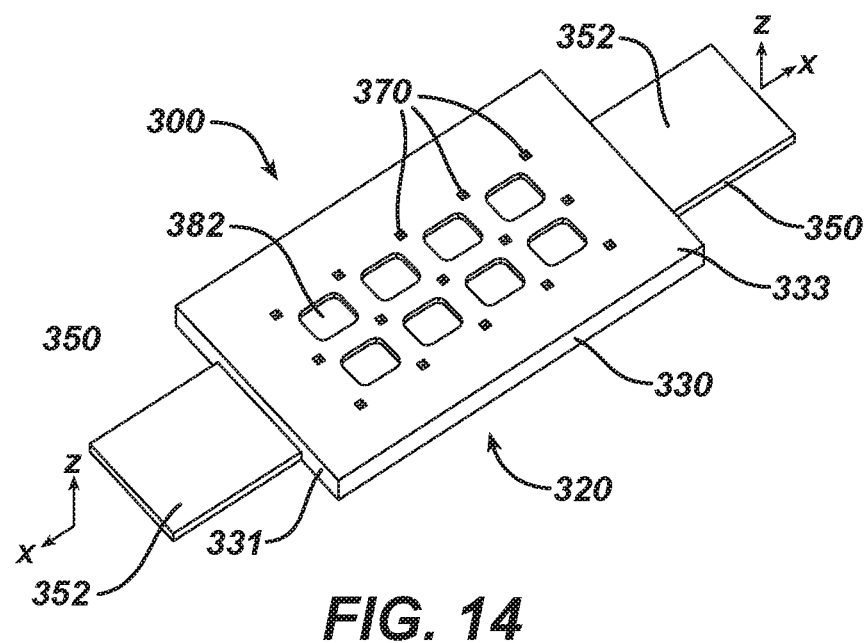
FIG. 14 is a top perspective view of the dual modality system embodiment of FIG. 13.
Figure 15:
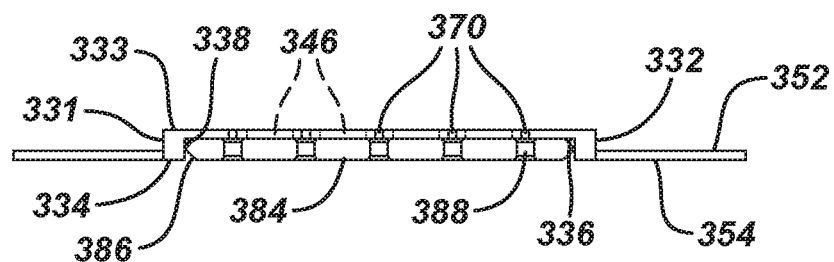
FIG. 15 is a cross-sectional view of the of the embodiment of FIG. 14 in the x-z plane.
Figure 16:
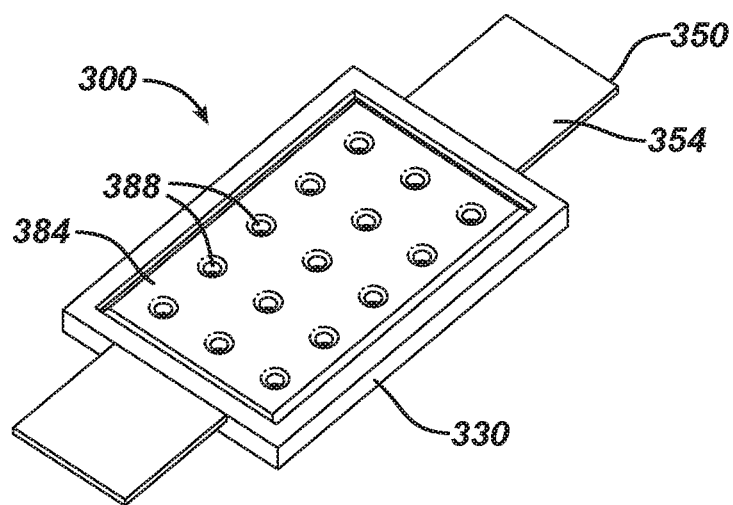
FIG. 16 is a bottom perspective view of the embodiment of FIG. 13.

Replaceable thermal subsystem 380 is coupled to the durable energy subsystem chassis 320 and arranged and configured to deliver thermal energy. FIGS. 14 and 16 are top and bottom, respectively, perspective views of dual modality system 300 when the system is assembled. FIG. 15 is a cross-sectional view of dual modality system 300 in the x-z plane of FIG. 14. When assembled, replaceable thermal subsystem 380 is disposed in the receptacle of main body 330 of durable energy subsystem chassis 320 so that first surface 382 of replaceable thermal subsystem 380 may at least partially contact receptacle bottom surface 336, and four side surfaces 386 of subsystem 380 may at least partially contact inner side surfaces 338. Apertures 388 of replaceable thermal subsystem 380 are disposed in the receptacle of main body 330 of durable energy subsystem chassis 320 so that they are aligned with energy emitters 370 of main body 330.

Replaceable thermal subsystem 380 is held in receptacle of main body 330 of durable energy subsystem chassis 320 by any number of means. These include friction fits between side surfaces 386 and receptacle inner side surfaces 338, or between first surface 382 and receptacle bottom surface 336. In some embodiments, an adhesive or other coupling feature may be used to hold replaceable thermal subsystem 380 in receptacle of main body 330. In other embodiments, replaceable thermal subsystem 380 is held in receptacle of main body 330 by being trapped between receptacle bottom surface 336 and the treatment area of the user when dual modality system 300 is in contact with the treatment area of a user's body.

In this embodiment, replaceable thermal subsystem 380 is in the shape of a rectangular prism. In other embodiments, replaceable thermal subsystem 380 may be in other three-dimensional shapes.

End tabs 350, disposed on first longitudinal end 331 and second longitudinal end 332 of main body 330, may be integral to, or attached to main body 330 of durable energy subsystem chassis 320. Attachment may be achieved using an adhesive, or welding the end tabs 350 to main body 330 if they are not formed as integral to main body 330 of durable energy subsystem chassis 320.

In addition, though energy emitters 370 are shown as disposed in or proximate to second surface 334 of main body 330, energy emitters 370 may be disposed on the surface of second surface 334 of main body 330. The number, shape and arrangement of energy emitters 370 in main body 330 will depend on the treatment type, intensity, and area being treated. The plurality of energy emitters 370 are disposed in an emission region of the chassis 320 having a length and a width, wherein the emission region length and emission region width are both substantially greater than an emission region depth.

In use, durable energy subsystem chassis 320 and the replaceable thermal subsystem 380 comprising dual modality system 300 are coupled to a desired treatment area of a user's body. In this embodiment, adhesive disposed on second surface 354 of end tabs 350 acts as a means to couple dual modality system 300 to a desired treatment area of a user's body. In use, second surface 384 of replaceable thermal subsystem 380 contacts the desired treatment area of a user's body.

In other embodiments, adhesive may also be disposed on second surface 334 of main body 330. In still other embodiments, end tabs 350 may not be present, and adhesive disposed on second surface 334 of main body 330 may act as a means to couple dual modality system 300 to the desired treatment area of a user's body.

The plurality of apertures 346 disposed on main body 330. The plurality of apertures 346 may provide air permeability or skin breathability to dual modality system 300. In some embodiments, main body 330 does not have apertures. In other embodiments, improved skin breathability may be achieved by main body 330 having a discontinuous skin-contact surface.

Though not shown, fourth embodiment dual modality system 300 may also have release paper disposed on the regions having adhesive. In use, the user would first place replaceable thermal subsystem 380 into receptacle of main body 330, remove any release paper covering regions having adhesive, and place the dual modality system 300 on the desired treatment area of a user's body. In this embodiment, replaceable thermal subsystem 380 is integrated with the means to couple durable energy subsystem chassis 320 and replaceable thermal subsystem 380 to a desired treatment area of a user's body. Operational details of durable energy subsystem chassis 320 will be discussed later in this document.

As discussed previously, dual modality system 300 may have various sizes and shapes depending on the location of use for system.

Figure 17:
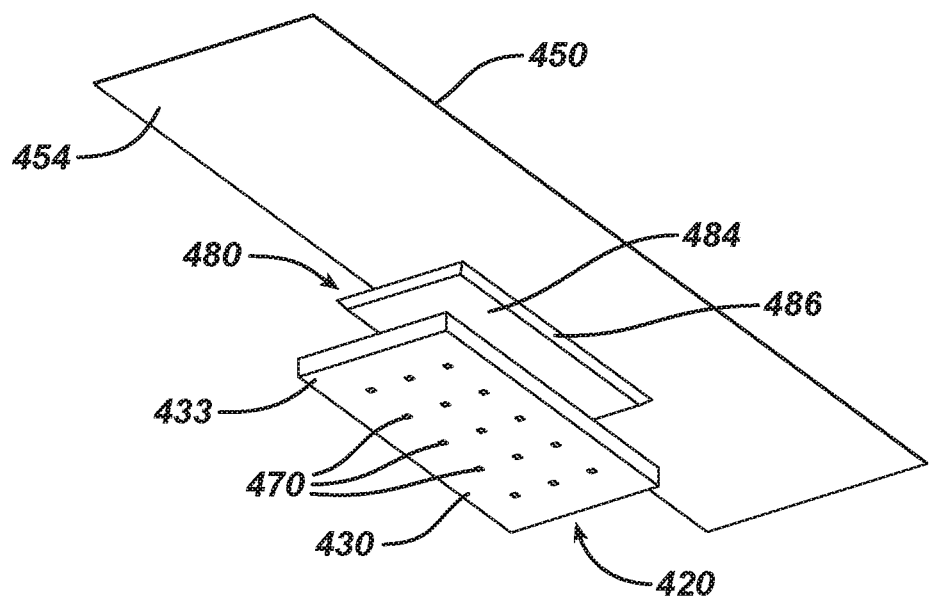
FIG. 17 is an exploded view of a fifth embodiment of a dual modality system of the present invention.

FIGS. 17 to 20 show a fifth embodiment of a dual modality system 400 of the present invention. FIG. 17 is an exploded view of dual modality system 400 which has a durable energy subsystem chassis 420, a replaceable thermal subsystem 480, and an adhesive band 450 to attach durable subsystems 420 and replaceable thermal subsystem 480 to the desired treatment area of a user's body. Replaceable thermal subsystem 480 has a first surface 482, a second surface 484, and four side surfaces 486, and may be a heat source or a cooling source.

Durable energy subsystem chassis 420 has a body 430. Body 430 has a first surface 433, a second surface 434, and a receptacle defined by bottom surface 436 and four inner side surfaces 438. Disposed in first surface 433 of body 430 are a plurality of energy emitters 470. In some embodiments, durable energy subsystem chassis 420 is flexible. Durable energy subsystem chassis 420 may optionally include at least one component arranged and configured to communicate data through wired or wireless communication with external devices, such as a smart phone or other computer or communication device connected to a network.

Adhesive band 450 has a first surface 452, and a second surface 454, and may be a flexible web.

Figure 18:
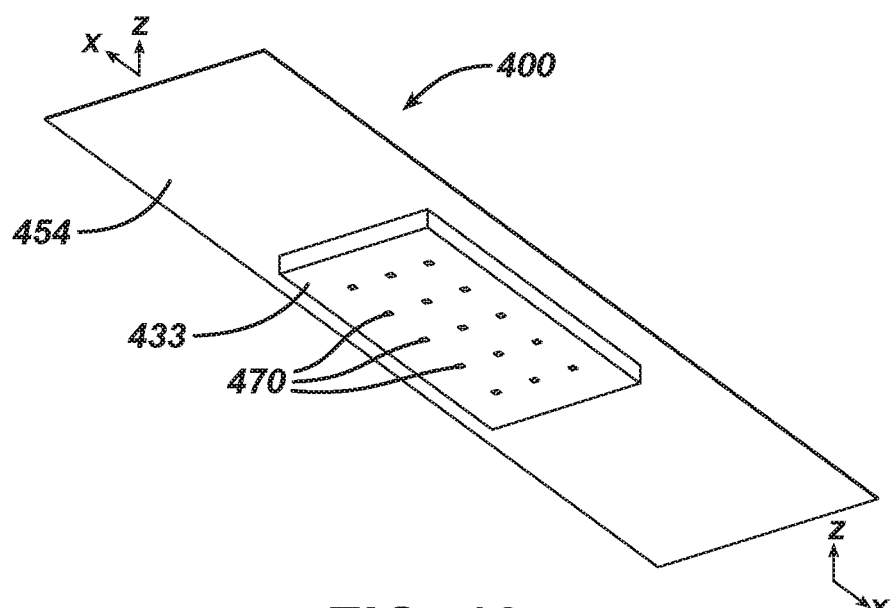
FIG. 18 is a top perspective view of the dual modality system embodiment of FIG. 17.
Figure 19:
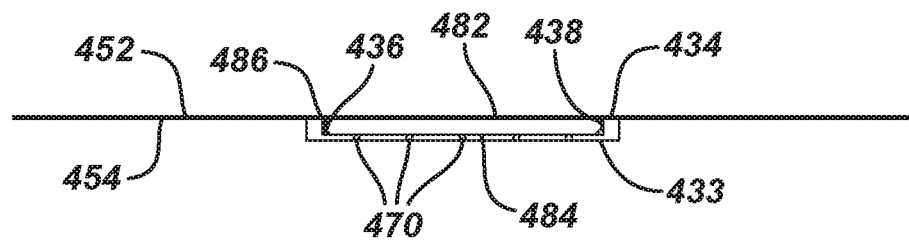
FIG. 19 is a cross-sectional view of the of the embodiment of FIG. 18 in the x-z plane.
Figure 20:
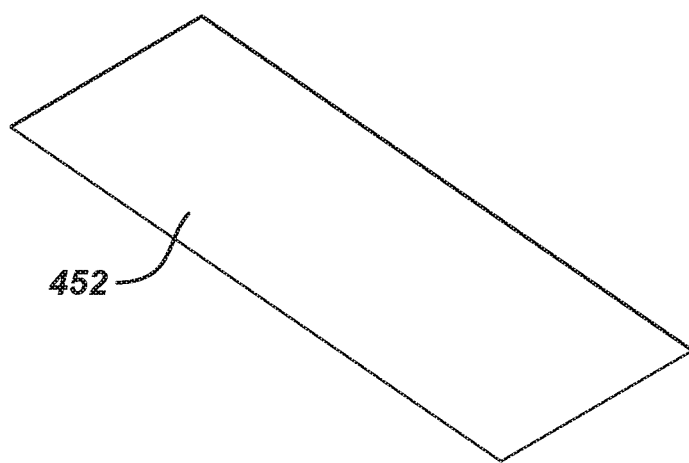
FIG. 20 is a bottom perspective view of the embodiment of FIG. 17.

Replaceable thermal subsystem 480 is coupled to the durable energy subsystem chassis 420 and arranged and configured to deliver thermal energy. FIGS. 18 and 20 are top and bottom, respectively, perspective views of dual modality system 400 when the system is assembled. FIG. 19 is a cross-sectional view of dual modality system 400 in the x-z plane of FIG. 18. When assembled, replaceable thermal subsystem 480 is disposed in the receptacle of main body 430 of durable energy subsystem chassis 420 so that second surface 484 of replaceable thermal subsystem 480 may at least partially contact receptacle bottom surface 436, and four side surfaces 486 of subsystem 480 may at least partially contact inner side surfaces 438.

Replaceable thermal subsystem 480 is held in receptacle of main body 430 of durable energy subsystem chassis 420 by any number of means. These include friction fits between side surfaces 486 and receptacle inner side surfaces 438. In other embodiments, an adhesive may be used to hold replaceable thermal subsystem 480 in receptacle of main body 430. In yet other embodiments, replaceable thermal subsystem 480 is held in receptacle of main body 430 by being trapped between receptacle bottom surface 436 and the treatment area of the user when dual modality system 400 is in contact with the treatment area of a user's body.

In this embodiment, replaceable thermal subsystem 480 is in the shape of a rectangular prism. In other embodiments, replaceable thermal subsystem 480 may be in other three-dimensional shapes.

In addition, though energy emitters 470 are shown as disposed in or proximate to second surface 434 of main body 430, energy emitters 470 may be disposed on the surface of second surface 434 of main body 430. The number, shape and arrangement of energy emitters 470 in main body 430 will depend on the treatment type, intensity, and area being treated. The plurality of energy emitters 470 are disposed in an emission region of the chassis 420 having a length and a width, wherein the emission region length and emission region width are both substantially greater than an emission region depth.

In use, durable energy subsystem chassis 420 and the replaceable thermal subsystem 480 comprising dual modality system 400 are coupled to a desired treatment area of a user's body. In this embodiment, adhesive disposed on second surface 454 of adhesive band 450 acts as a means to couple dual modality system 400 to a desired treatment area of a user's body. In use, first surface 433 of main body 430 contacts the desired treatment area of a user's body. In some embodiments, adhesive may also be disposed on first surface 433 of main body 430. Second surface 454 of adhesive band 450 contacts first surface 482 of replaceable thermal subsystem 480, second surface 434 of main body 430, and the user's skin.

Though not shown, fifth embodiment dual modality system 400 may also have release paper disposed on the regions having adhesive. In use, the user would first dispose replaceable thermal subsystem 480 into receptacle of main body 430, remove any release paper covering regions having adhesive, dispose adhesive band 450 on replaceable thermal subsystem 480 and main body 430, and place the dual modality system 400 on the desired treatment area of a user's body so that durable energy subsystem 420 and replaceable thermal subsystem 480 are coupled to a desired treatment area of a user's body with a flexible web (adhesive band 450) having an adhesive surface.

In an alternative embodiment use, the user would first dispose replaceable thermal subsystem 480 is affixed to dispose adhesive band 450 prior to being disposed into receptacle of main body 430. Dual modality system 400 is then placed on the desired treatment area of a user's body so that durable energy subsystem 420 and replaceable thermal subsystem 480 are coupled to a desired treatment area of a user's body with a flexible web (adhesive band 450) having an adhesive surface.

Operational details of durable energy subsystem chassis 420 will be discussed later in this document.

Figure 21:
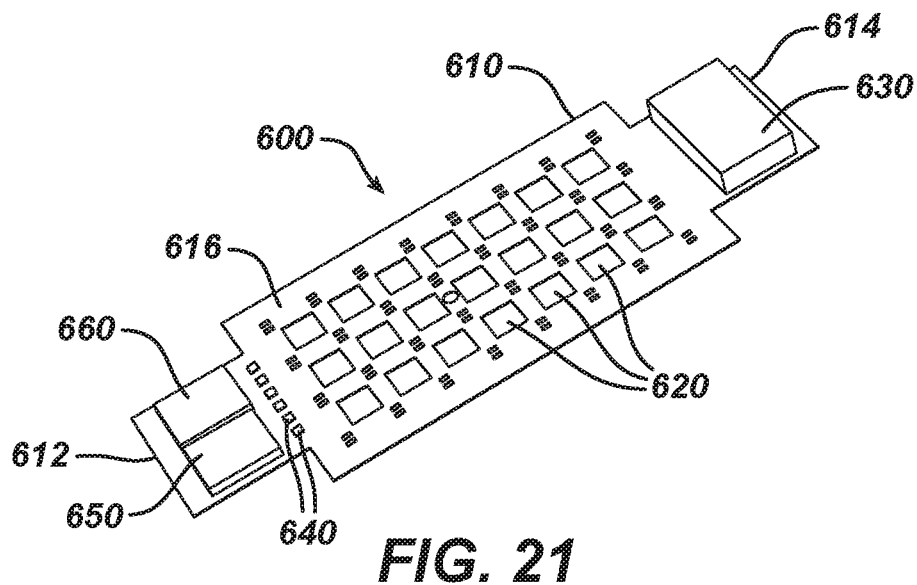
FIG. 21 is a top perspective view of a first embodiment of a durable energy subsystem of the present invention.
Figure 22:
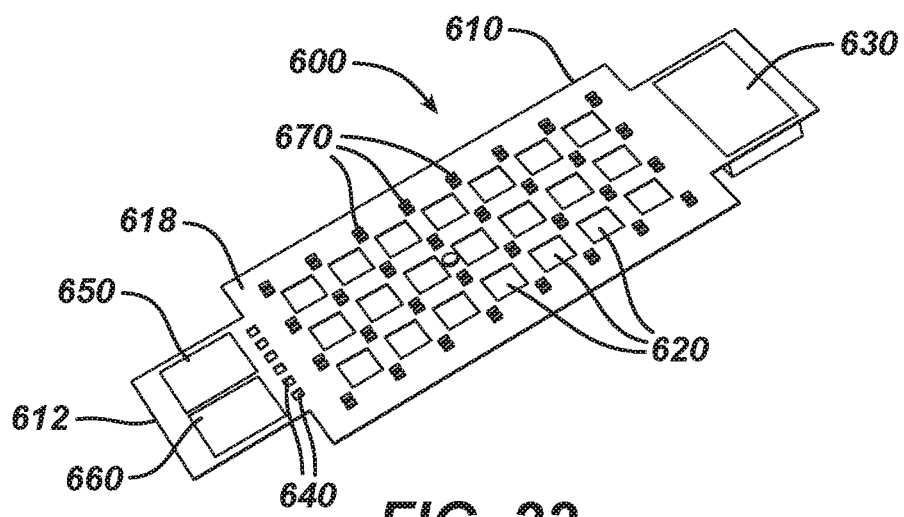
FIG. 22 is a bottom perspective view of the durable energy subsystem embodiment of FIG. 21.

As mentioned earlier, durable energy subsystem chassis (20, 120, 220, 320, or 420) are arranged and configured to deliver energy. FIGS. 21 to 24 show two detailed embodiments of durable energy subsystem chassis. FIGS. 21 and 22 are top and bottom, respectively, perspective views of a first embodiment of a durable energy subsystem 600. Durable energy subsystem 600 includes a main body 610 with a first longitudinal end 612, a second longitudinal end 614, a first surface 616 and a second surface 618. Apertures 620 through main body 610 provide air permeability and/or skin breathability and light weight to the dual modality system using energy subsystem 600.

In this embodiment, main body 610 is a printed circuit board (PCB). A PCB mechanically supports and electrically connects electronic components using conductive tracks, pads and other features etched from copper sheets laminated onto a non-conductive substrate. Components (e.g. capacitors, resistors, controllers, or active devices) are generally soldered on the PCB. This embodiment uses an advanced PCB board in which may of the components are embedded in main body 610 substrate. In this embodiment, main body 610 is flexible, so that it can conform to the treatment area of a user's body.

A controller or set of controllers in the durable energy subsystem 600 are used to control the energy delivery from durable energy subsystem 600 to desired treatment area of a user's body. The energy from the dual modality system may be delivered continuously, discontinuously, or may be delivered intermittently.

Embedded in and exposed on first surface 616 of main body 610 are a power source 630, contacts 640, charging module 650 and signal send/receive unit 660. Embedded in and exposed on second surface 618 of main body 610 are a plurality of energy emitters 670. The plurality of energy emitters 670 are disposed in an emission region of main body 610 having a length and a width, wherein the emission region length and emission region width are both substantially greater than an emission region depth. Power source 630 is typically batteries, which in this embodiment are rechargeable using charging module 650. Durable energy subsystem 600 may optionally include at least one component arranged and configured to communicate data through wired or wireless communication with external devices, such as a smart phone or other computer or communication device connected to a network.

Energy emitters 670 may comprise one or more electromagnetic radiation emitters/modalities. These include, but are not limited to, light, electromagnetic field, microcurrent, electrical stimulation (TENS trans-cutaneous electrical nerve stimulation, MENS, PENS), iontophoresis, sonophoresis (require additional element, topical, active, etc.). In some embodiments, energy emitters 670 may emit light in the form of visible, ultra-violet (UV), or Infra-Red (IR) light. In other embodiments, energy emitters 670 may comprise one or more physical motion emitters including without limitation ultrasound, vibration, and combinations thereof.

In first embodiment durable energy subsystem 600 presented here, energy emitters 670 are light-emitting diode (LED) pairs. By pairing the LEDs, LEDs of a variety of wavelengths can be used to delivery light energy to the same location. In this embodiment, thirty-two pairs of LEDs are partially embedded in main body 610 of energy subsystem 600. They are arrayed in an 8-by-4 rectangular pattern. In other embodiments, there may be more or fewer energy emitters 670, and they may be arranged in square, triangular, or other patterns, or may be randomly arranged in main body 610. The number of energy emitters 670 in durable energy subsystem 600 could be 1, or 2, or 5, or 10, or 20 or 100 or more.

While the above description references pairs of LEDs, the light emitter may include LEDs as well as incandescent light bulbs, halogen lamps, lasers, fluorescent lamps, plasma lamps, or combinations of the above.

Durable energy subsystem 600 may be designed to deliver a variety of irradiances (measured in watts/centimeter$^2$), or, preferably, irradiance doses (measured in Joules/centimeter$^2$). The number and layout of energy emitters 670 will affect the irradiance or irradiance dose of durable energy subsystem 600. In a preferred embodiment, the light emitter provides at least about 1 J/cm$^2$, more preferably, at least about 5 J/cm$^2$. A preferred range is between about 5 J/cm$^2$ and about 50 J/cm$^2$, more preferably, between about 5 J/cm$^2$ and about 20 J/cm$^2$, and most preferably, between about 5 J/cm$^2$ and about 15 J/cm$^2$, and even between about 8 J/cm$^2$ and about 12 J/cm$^2$.

Figure 23:
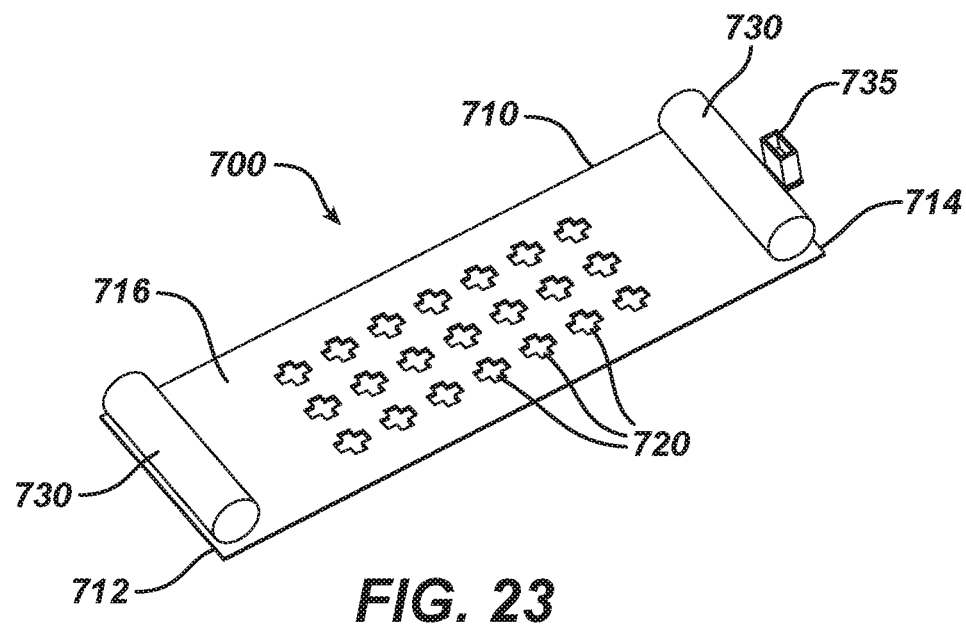
FIG. 23 is a top perspective view of a second embodiment of a durable energy subsystem of the present invention.
Figure 24:
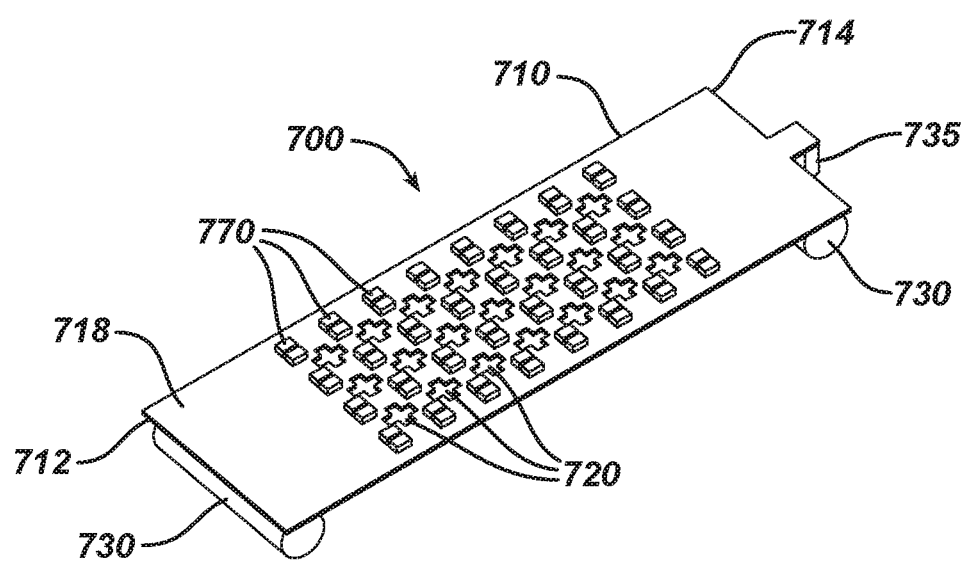
FIG. 24 is a bottom perspective view of the durable energy subsystem embodiment of FIG. 23.

FIGS. 23 and 24 are top and bottom, respectively, perspective views of a second embodiment of a durable energy subsystem 700. Durable energy subsystem 700 includes a main body 710 with a first longitudinal end 712, a second longitudinal end 714, a first surface 716 and a second surface 718. Apertures 720 through main body 710 provide air permeability or skin breathability and light weight to the dual modality system using energy subsystem 700.

Similar to the first embodiment, main body 710 is an advanced printed circuit board (PCB), where many of the components are embedded in main body 710 substrate. In addition, main body 710 is flexible, so that it can conform to the treatment area of a user's body.

A controller or set of controllers in the durable energy subsystem 700 are used to control the energy delivery from durable energy subsystem 700 to desired treatment area of a user's body. The energy from the dual modality system may be delivered continuously, discontinuously, or may be delivered intermittently. Durable energy subsystem 700 may optionally include at least one component arranged and configured to communicate data through wired or wireless communication with external devices, such as a smart phone or other computer or communication device connected to a network.

In this embodiment, the power source 730 on first surface 716 of main body 710 are battery enclosures which each include a rechargeable battery. In this embodiment, the batteries are rechargeable using charger clip 735 which is disposed on second longitudinal end 714 of main body 710. In this embodiment, the battery enclosures are substantially cylindrical.

In this embodiment, energy emitters 770 are light-emitting diode (LED) pairs. As mentioned earlier, pairing the LED allows durable energy subsystem 700 to delivery light energy of different wavelengths to the same location. In this embodiment, thirty-two pair of LEDs are disposed on second surface 718 of main body 710 of energy subsystem 700. They are arrayed in an 8-by-4 rectangular pattern defining an emission region of the main body 710 having a length and a width, wherein the emission region length and emission region width are both substantially greater than an emission region depth. In other embodiments, there may be more or fewer energy emitters 770, and they may be arranged in square, triangular, or other patterns, or may be randomly arranged in main body 710. The number of energy emitters 770 are in durable energy subsystem 700 could be 1, or 2, or 5, or 10, or 20 or 100 or more.

In the above embodiments, durable energy subsystems 600 and 700 are advanced printed circuit boards (PCBs). In some embodiments, there may be a desire to protect the PCBs from the outside environment, especially moisture, salt, chemicals and temperature changes. For their protection, durable energy subsystems 600 and 700 may be encased in a protective, or conformal, coating material. Conformal coating material is a thin polymeric film which 'conforms' to the contours of a printed circuit board to protect the board's components. Typically applied at 25-250 micrometers it is applied to electronic circuitry to act as protection against moisture, dust, chemicals, and temperature extremes. Conformal coatings are also "breathable", allowing trapped moisture in electronic boards to escape while maintaining protection from environmental contaminates. However, these coatings are not sealants, and prolonged exposure to vapors will cause transmission and degradation to occur.

Some of the materials which may be used as conformal coatings include, but are not limited to: acrylics, epoxies, polyurethanes, silicones, and fluoropolymers. The coating material can be applied by various methods, from brushing, spraying and dipping.

Figure 25:
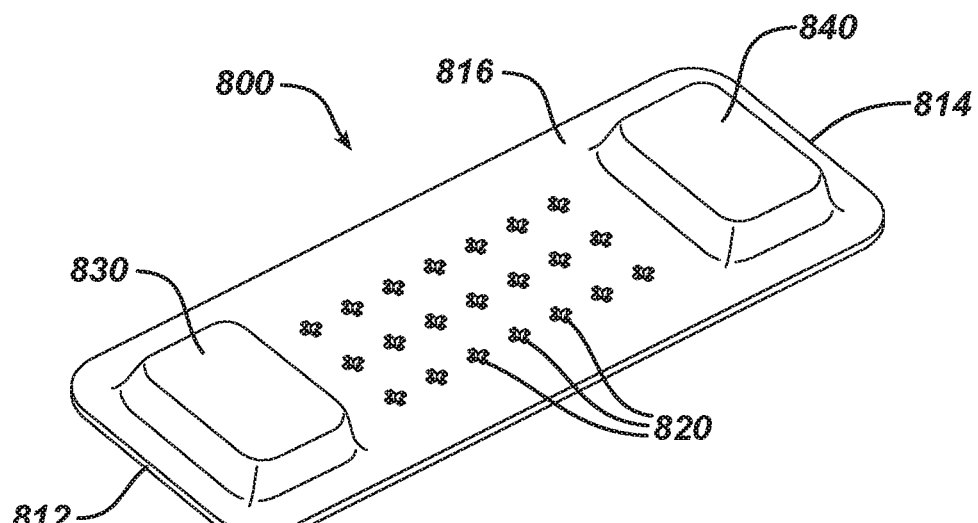
FIG. 25 is a top perspective view of an embodiment of a durable energy subsystem of the present invention encased in a protective coating.
Figure 26:
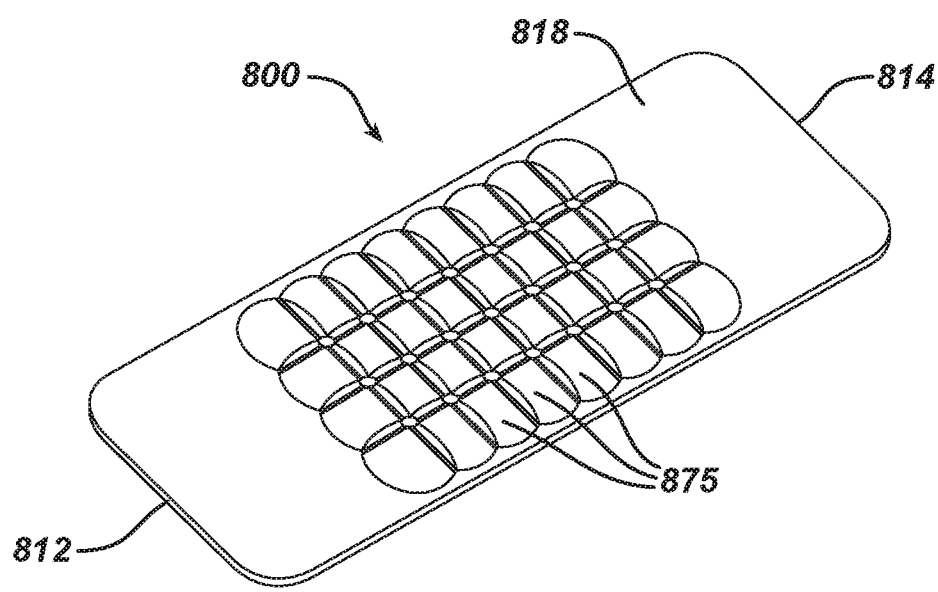
FIG. 26 is a bottom perspective view of the encased durable energy subsystem embodiment of FIG. 25.

FIGS. 25 and 26 show an embodiment of a durable energy subsystem 600 encased in a protective coating. FIG. 25 is a top perspective view of encased 800 durable energy subsystem 600, while FIG. 26 is a bottom perspective view of encased 800 durable energy subsystem 600.

The figures show encased 800 durable energy subsystem 600 has a first longitudinal end 812, a second longitudinal end 814, a first surface 816, a second surface 818, a plurality of apertures 820, raised regions 830 and 840 disposed on first surface 816, and raised regions 875 disposed on second surface 818.

Located under raised region 830 is power source 630. Charging module 650 and signal send/receive unit 660 are located under raised region 840. Energy emitters 670 are located under raised regions 875. In some embodiments, raised regions 875 act as lenses to focus, or scatter the energy from energy emitters 670. In addition, raised regions 875 act as spacers between encased 800 durable energy subsystem 600 and the treatment area of a user's body. Durable energy subsystem 600 may optionally include at least one component arranged and configured to communicate data through wired or wireless communication with external devices, such as a smart phone or other computer or communication device connected to a network.

Figure 27:
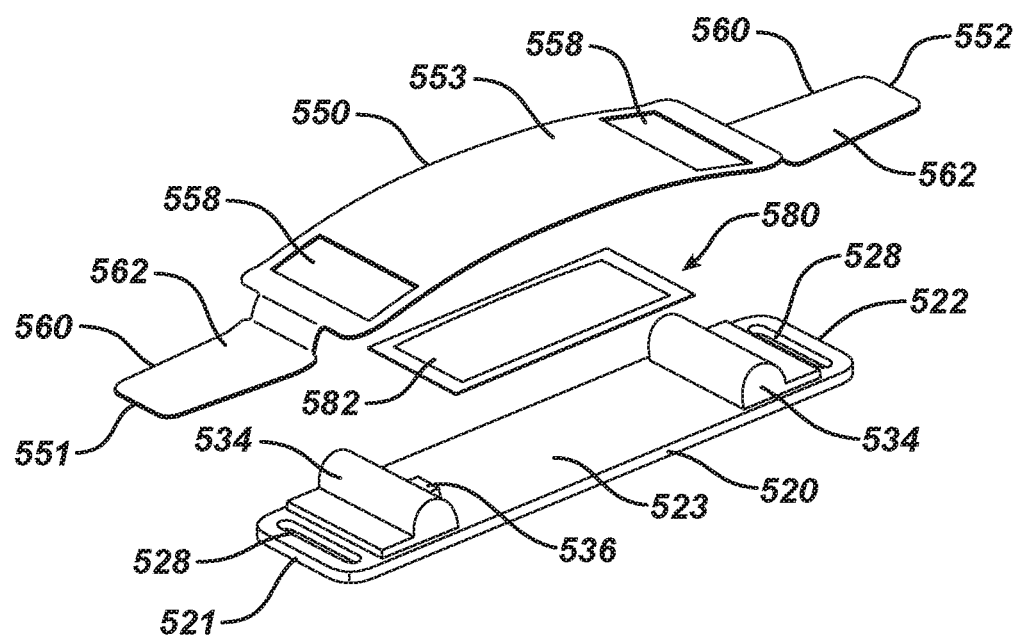
FIG. 27 is an exploded view of a sixth embodiment of a dual modality system of the present invention.

FIGS. 27 to 30 show a sixth embodiment of a dual modality system 500 of the present invention. FIG. 27 is an exploded view of dual modality system 500 which has a durable energy subsystem chassis 520, a replaceable thermal subsystem 580, and a flexible web, such as a belt or strap 550 to attach subsystems 520 and replaceable thermal subsystem 580 to the desired treatment area of a user's body. Replaceable thermal subsystem 580 has a first surface 582, and a second surface 584, and may be a heat source or a cooling source.

Durable energy subsystem chassis 520 has a first longitudinal end 521, a second longitudinal end 522, a first surface 523, a second surface 524, and slots 528 located near first and second ends 521, 522. Disposed on first surface 523 of durable energy subsystem chassis 520, are power source/control modules 534 and charging module 536. In some embodiments, durable energy subsystem chassis 520 is flexible.

Belt 550 has a first longitudinal end 551, a second longitudinal end 552, a first surface 553, a second surface 554, and slots 558 positioned to align with power source/control modules 534 located on surface 523 of durable energy subsystem chassis 520, End tabs 560 are preferably flexible and are disposed on first longitudinal end 551 and second longitudinal end 552 of belt 550. End tabs 560 each have a first surface 562, and a second surface 564.

Figure 28:
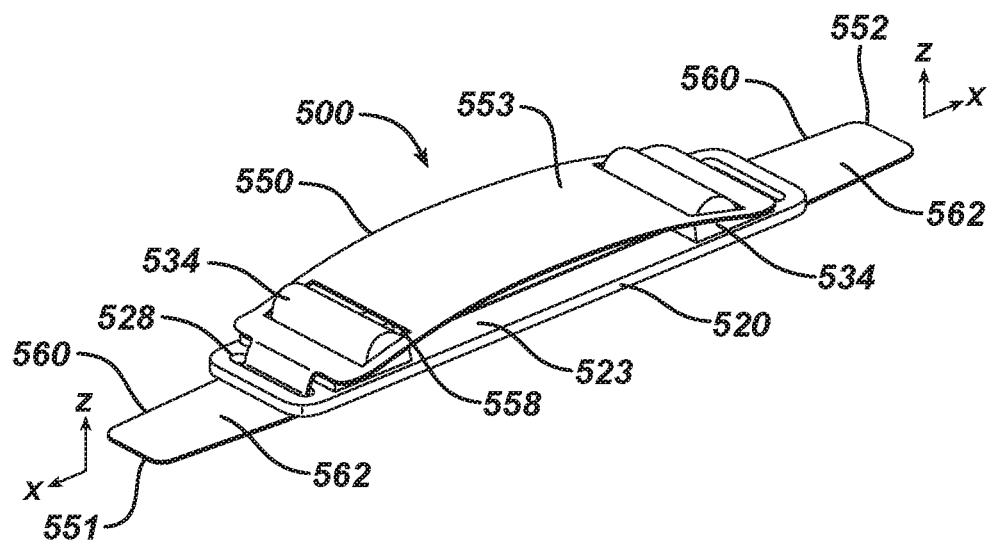
FIG. 28 is a top perspective view of the dual modality system embodiment of FIG. 27.
Figure 29:
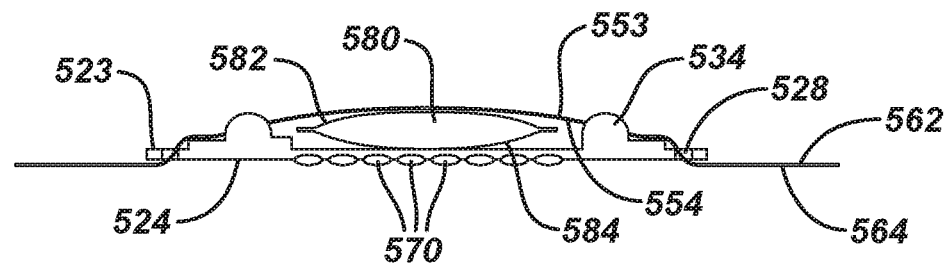
FIG. 29 is a cross-sectional view of the of the embodiment of FIG. 28 in the x-z plane.
Figure 30:
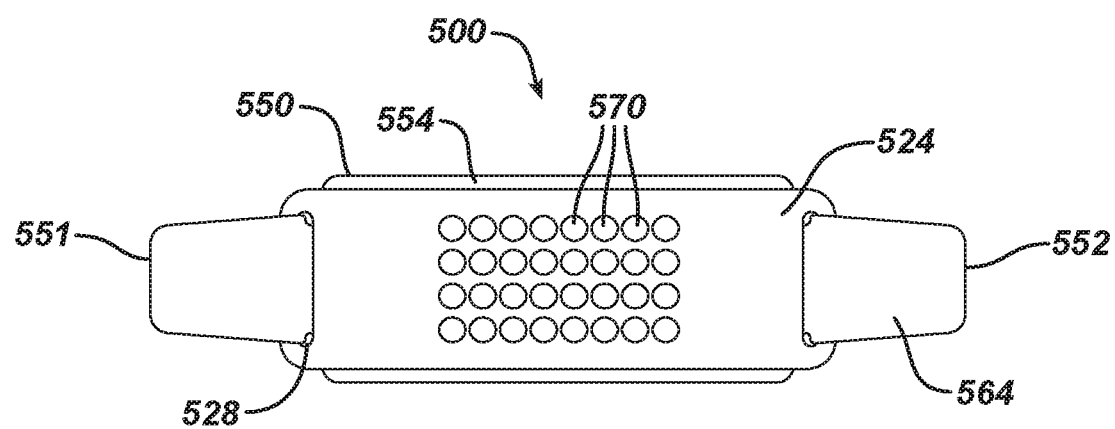
FIG. 30 is a bottom view of the embodiment of FIG. 27.

Replaceable thermal subsystem 580 is coupled to the durable energy subsystem chassis 520 and arranged and configured to deliver thermal energy. FIG. 28 is a top perspective view of dual modality system 500 when the system is assembled. FIG. 29 is a cross-sectional view of dual modality system 500 in the x-z plane of FIG. 28. When assembled, replaceable thermal subsystem 580 is disposed between durable energy subsystem chassis 520 and belt 550 so that second surface 584 of replaceable thermal subsystem 580 contacts first surface 523 of chassis 520 and first surface 582 of replaceable thermal subsystem 580 contacts second surface 554 of belt 550. In addition, when dual modality system 500 is assembled, end tabs 560 of belt 550 are woven through slots 528 of durable energy subsystem chassis 520. Slots 558 of belt 550 are positioned to allow power source/control modules 534 located on surface 523 of durable energy subsystem chassis 520 to pass through them, giving dual modality system 500 additional stability.

Replaceable thermal subsystem 580 is held on durable energy subsystem chassis 520 by any number of means. These include friction fits between second surface 584 of replaceable thermal subsystem 580 and first surface 523 of chassis 520 and between first surface 582 of replaceable thermal subsystem 580 and second surface 554 of belt 550. In other embodiments, an adhesive may be used to hold replaceable thermal subsystem 580 to belt 550.

In this embodiment, replaceable thermal subsystem 580 is in the shape of a rectangular prism. In other embodiments, replaceable thermal subsystem 580 may be in other three-dimensional shapes.

Energy emitters 570 are shown as disposed in or proximate to second surface 524 of durable energy subsystem chassis 520. In other embodiments, energy emitters 570 may be disposed on the surface of second surface 524 of durable energy subsystem chassis 520. The number, shape and arrangement of energy emitters 570 in replaceable thermal subsystem 580 will depend on the treatment type, intensity, and area being treated.

In use, durable energy subsystem chassis 520 and the replaceable thermal subsystem 580 comprising dual modality system 500 are coupled to a desired treatment area of a user's body. In this embodiment, adhesive disposed on second surface 564 of tabs 560 of belt 550 acts as a means to couple dual modality system 500 to a desired treatment area of a user's body. In use, second surface 524 of durable energy subsystem chassis 520 contacts the desired treatment area of a user's body. In some embodiments, adhesive may also be disposed on second surface 524 of durable energy subsystem chassis 520. Second surface 564 of tabs 560 contacts the user's skin.

Though not shown, sixth embodiment dual modality system 500 may also have release paper disposed on the regions having adhesive. In use, the user would first dispose replaceable thermal subsystem 580 onto first surface 523 of durable energy subsystem chassis 520. Then user weaves, or laces end tabs 560 of belt 550 through slots 528 of durable energy subsystem chassis 520. In the next step, user removes any release paper covering regions having adhesive, and places the dual modality system 500 on the desired treatment area of a user's body so that durable energy subsystem 520 and replaceable thermal subsystem 580 are coupled to a desired treatment area of a user's body with a flexible web (belt 550) having an adhesive surface. Operational details of durable energy subsystem chassis 520 are similar to those previously discussed for durable energy subsystem chassis (20, 120, 220, 320, and 420).

Although in this embodiment adhesive disposed on second surface 564 of tabs 560 of belt 550 acts as a means to couple dual modality system 500 to a desired treatment area of a user's body, there are other possible a means to couple dual modality system 500 to a desired treatment area of a user's body. These include a wrap, sleeve, band, mechanical attachment, belt, laces, and combinations thereof.

Figure 31:
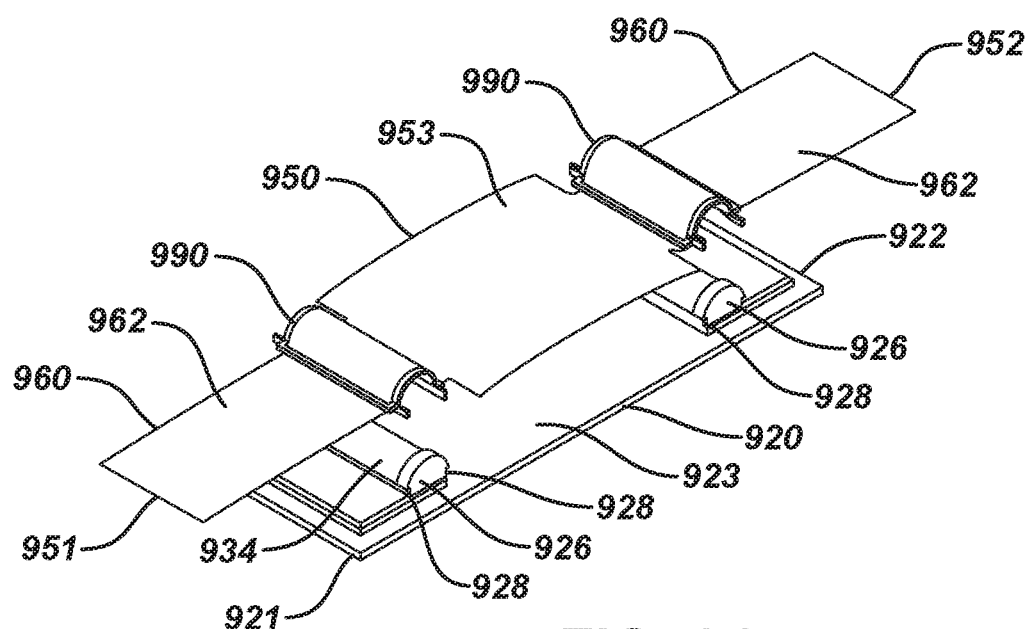
FIG. 31 is an exploded view of a seventh embodiment of a dual modality system of the present invention.

FIGS. 31 to 36 show a seventh embodiment of a dual modality system 900 of the present invention. FIG. 31 is an exploded view of dual modality system 900 which has a durable energy subsystem chassis 920, a replaceable thermal subsystem 980, a flexible web, such as a belt or strap 950 to attach subsystems 920 and replaceable thermal subsystem 980 to the desired treatment area of a user's body, and clips 990 to attach belt 950 to durable energy subsystem chassis 920. Replaceable thermal subsystem 980 has a second surface 984 and may be a heat source or a cooling source.

Durable energy subsystem chassis 920 has a first longitudinal end 921, a second longitudinal end 922, a first surface 923, and a second surface (not shown). Disposed on first surface 923 of durable energy subsystem chassis 920, are power source/control modules 934 and attachment caps 926 with detents 928. In this embodiment, the power sources 934 are batteries located in battery enclosures which are substantially cylindrical. Durable energy subsystem chassis 920 may optionally include at least one component arranged and configured to communicate data through wired or wireless communication with external devices, such as a smart phone or other computer or communication device connected to a network.

Belt 950 has a first longitudinal end 951, a second longitudinal end 952, a first surface 953 and a second surface 954. End tabs 960 are preferably flexible and are disposed on first longitudinal end 951 and second longitudinal end 952 of belt 950. End tabs 560 each have a first surface 962, and a second surface 964.

Figure 33:
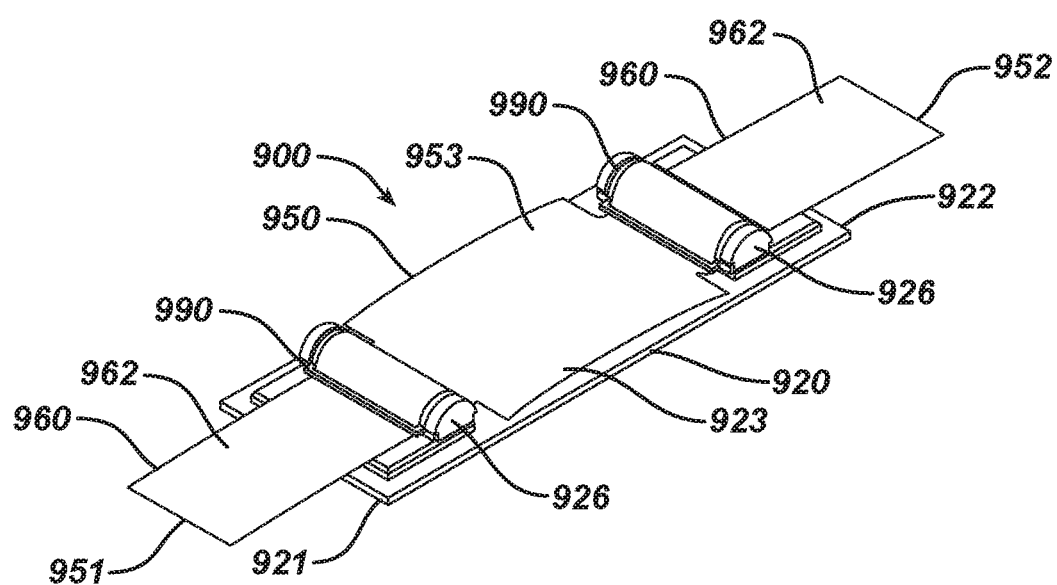
FIG. 33 is a top perspective view of the dual modality system embodiment of FIG. 31.

Replaceable thermal subsystem 980 is coupled to the durable energy subsystem chassis 920 and arranged and configured to deliver thermal energy. FIG. 33 is a top perspective view of dual modality system 900 when the system is assembled. When assembled, replaceable thermal subsystem 980 is disposed between durable energy subsystem chassis 920 and belt 950 so that second surface 984 of replaceable thermal subsystem 980 contacts first surface 923 of chassis 920 and first surface of replaceable thermal subsystem 980 contacts second surface 954 of belt 950.

Figure 34:
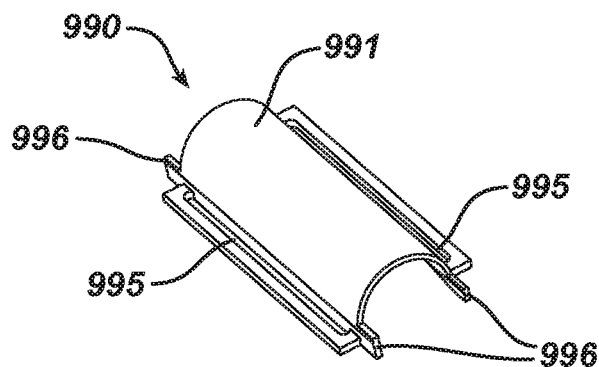
FIG. 34 is a top perspective view of a clip used in the seventh embodiment.

FIG. 34 is a top perspective view of clip 990. Clip 990 has a first surface 991, a second surface 993, slots 995, and tabs 996. When dual modality system 900 is assembled, end tabs 960 of belt 950 are woven through slots 995 of clips 990. Clips 990 define the means of attaching belt 950 to the durable energy subsystem chassis 920 in this embodiment.

Figure 35:
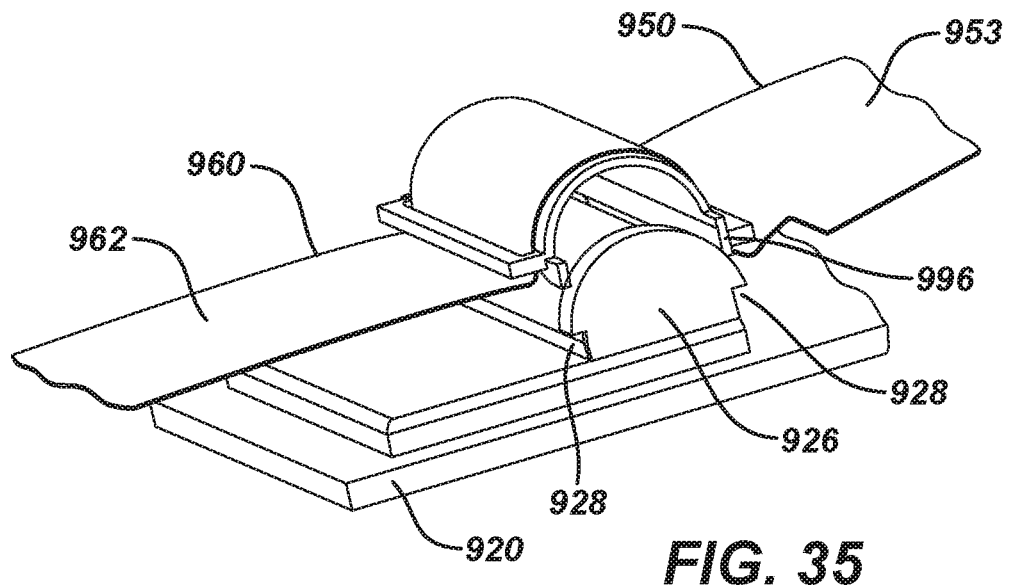
FIG. 35 is a top perspective view of the attachment means of the belt to the durable energy subsystem chassis in the seventh embodiment prior to engagement.
Figure 36:
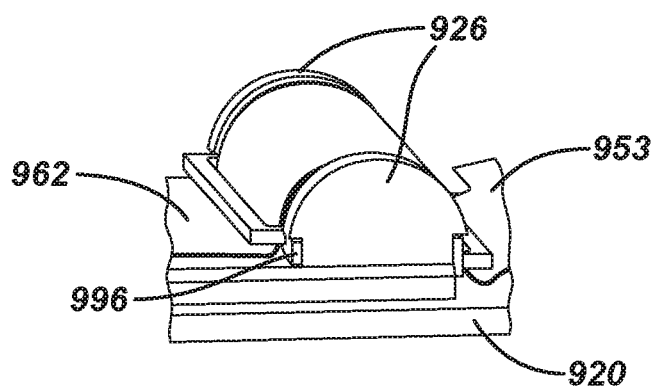
FIG. 36 is a top perspective view of the attachment means of the belt to the durable energy subsystem chassis in the seventh embodiment when engaged.

FIGS. 35 and 36 show how clip 990 is used to attach belt 950 to durable energy subsystem chassis 920. FIG. 35 is prior to engagement, while and FIG. 36 shows attachment. In FIG. 35, end tabs 960 of belt 950 are shown as woven through slots 995 of clip 990. Clip 990 is then pressed down onto and attachment caps 926. The body of clip 990 is resilient so that component 990 has a spring-like opening. Finally, tabs 996 of clip 990 engage with detents 928 of attachment caps 926 as shown in FIG. 36. In this embodiment, clip 990 corresponds to the shape of the battery enclosure 934.

Replaceable thermal subsystem 980 is held on durable energy subsystem chassis 920 by any number of means. These include friction fits between second surface 984 of replaceable thermal subsystem 980 and first surface 923 of chassis 920 and between the first surface of replaceable thermal subsystem 980 and second surface 954 of belt 950. In other embodiments, an adhesive may be used to hold replaceable thermal subsystem 980 replaceable thermal subsystem 980 and belt 950.

In this embodiment, replaceable thermal subsystem 980 is in the shape of a rectangular prism. In other embodiments, replaceable thermal subsystem 980 may be in other three-dimensional shapes. Though not shown in the figures, durable energy subsystem chassis 920 has energy emitters in number, shape and arrangement as discussed in previous durable energy subsystems in this disclosure. Again, the energy emitters define an emission region of the chassis 920 having a length and a width, wherein the emission region length and emission region width are both substantially greater than an emission region depth.

In use, durable energy subsystem chassis 920 and the replaceable thermal subsystem 980 comprising dual modality system 900 are coupled to a desired treatment area of a user's body. In this embodiment, adhesive disposed on second surface 964 of tabs 960 of belt 950 acts as a means to couple dual modality system 900 to a desired treatment area of a user's body. In use, the second surface of durable energy subsystem chassis 920 contacts the desired treatment area of a user's body. In some embodiments, adhesive may also be disposed on the second surface of durable energy subsystem chassis 920. Second surface 964 of tabs 960 contacts the user's skin.

Though not shown, seventh embodiment dual modality system 900 may also have release paper disposed on the regions having adhesive.

Figure 32:
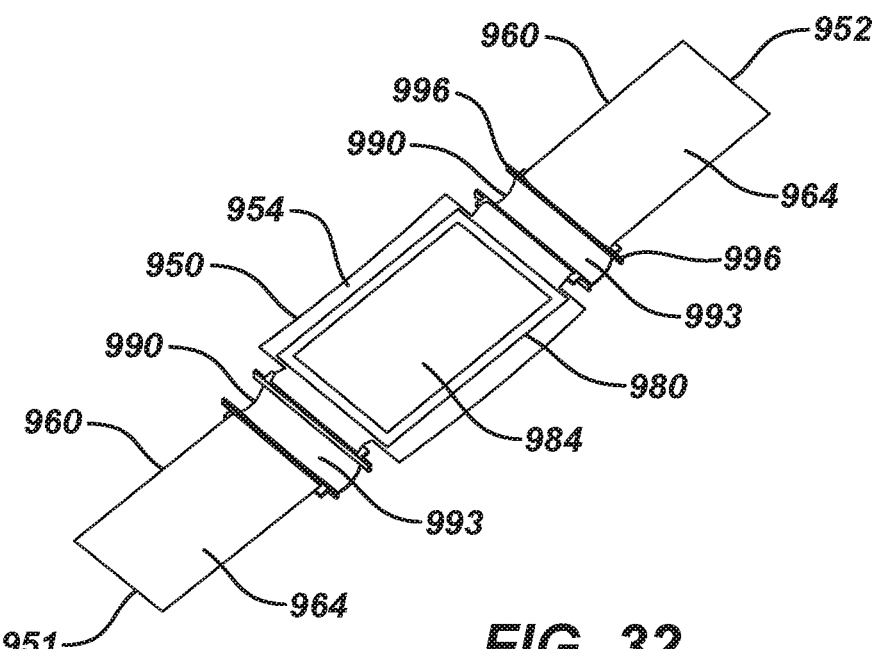
FIG. 32 is a bottom perspective view of the belt or strap component of the seventh embodiment.

In this embodiment, belt 950, replaceable thermal subsystem 980, and clips 990 are shown as preassembled (see FIGS. 31 and 32). In other embodiments, user would partially, or fully assemble the components before attaching them to replaceable thermal subsystem 980. In these embodiments, clips 990 are reusable.

In one embodiment of use, the user would first place replaceable thermal subsystem 980 onto first surface 923 of durable energy subsystem chassis 920. Then user weaves, or laces end tabs 960 of belt 950 through slots 995 of clips 990. Next, user attaches belt 950 to durable energy subsystem chassis 920 using clips 990 as discussed above. In the next step, user removes any release paper covering regions having adhesive, and places the dual modality system 900 on the desired treatment area of a user's body, so that durable energy subsystem 920 and replaceable thermal subsystem 980 are coupled to a desired treatment area of a user's body with a flexible web (belt 950) having an adhesive surface. Operational details of durable energy subsystem chassis 920 are similar to those previously discussed for durable energy subsystem chassis (20, 120, 220, 320, 420 and 520).

Although in this embodiment adhesive disposed on second surface 964 of tabs 960 of belt 950 acts as a means to couple dual modality system 900 to a desired treatment area of a user's body, there are other possible a means to couple dual modality system 900 to a desired treatment area of a user's body. These include a wrap, sleeve, band, mechanical attachment, belt, laces, and combinations thereof.

Replaceable thermal subsystems 80, 180, 280, 380, 480, 580, and 980 are arranged and configured to deliver thermal energy. Replaceable thermal subsystems may comprise one or more heating or cooling sources in which can generate heat or cold by chemical or physical means. For a replaceable thermal subsystem which delivers heat, the replaceable thermal subsystems employ a one-time exothermic chemical reaction. In some embodiments, heat generation is triggered by unwrapping an air-tight packet containing slightly moist iron powder and salt or catalysts which oxidizes over a period of hours after being exposed to oxygen in the air. Another type contains separate compartments within the replaceable thermal subsystem; when the user squeezes the replaceable thermal subsystem, a barrier ruptures and the compartments mix, producing heat such as the enthalpy change of solution of calcium chloride dissolving.

Phase change materials (PCMs) can also be used for replaceable thermal subsystem which deliver heat. The heat of fusion is used to release the thermal energy. Heat is released when the material changes from solid to liquid or vice versa.

For a replaceable thermal subsystem which delivers cooling, the replaceable thermal subsystems employ a one-time endothermic chemical reaction. In some embodiments, replaceable thermal subsystem consists of two bags; one containing water, inside a bag containing ammonium nitrate, calcium ammonium nitrate or urea. Cold generation is triggered when the inner bag of water is broken by squeezing the package, allowing the solid to dissolve in the water in an endothermic reaction. This reaction absorbs heat from the surroundings, quickly lowering the pack's temperature.

Phase change materials can also be used for replaceable thermal subsystem which deliver cooling. The heat of fusion is used to release the thermal energy. Cooling occurs when the material changes from solid to liquid or vice versa.

As mentioned in some embodiments, the dual modality systems of the disclosed invention are coupled to a desired treatment area of a user's body using adhesives. In some embodiments, water soluble bioadhesive polymers can be used for skin adhesive properties. Examples useful for the invention include, but are not limited to, cellulose and its derivatives, polyvinyl pyrrolidone, water soluble celluloses, polyvinyl alcohol, ethylene maleic anhydride copolymer, methylvinyl ether maleic anhydride copolymer, acrylic acid copolymers, anionic polymers of methacrylic acid and methacrylate, cationic polymers with dimethyl-aminoethyl ammonium functional groups, polyethylene oxides, water soluble polyamide or polyester, polyethylene glycol, water soluble acrylic polymers, water soluble polyesters, hydroxyalkyl starches, casein, gelatin, solubilized proteins, polyacrylamide, polyamines, polyquarternium amines, styrene maleic anhydride resins, polyethylene amines. The water soluble carbohydrate can form hydrogen or covalent bonding to the water soluble or hydrophilic polymer in the film.

In some embodiments, the dual modality system described above may have one or more sensors to indicate conditions at the treatment area. The one or more sensors may be disposed on or in either the durable energy subsystem chassis, or the replaceable thermal subsystem. In some embodiments, the one or more sensors may be a thermal sensor. In these embodiments, the dual modality system may also have an indicator, such as a display, to report of out-of-range thermal conditions. In a preferred embodiment, the "out-of-range thermal condition" may be set to permit a maximum operating temperature at the skin of about 45° C. Or the dual modality system may have a controller to shut down the system or alter elements of the system to maintain the desired conditions at the treatment area.

While in most of the foregoing embodiments, the replaceable thermal subsystem 80, 180, 280, 380, 480, 580, and 980 may be in other three-dimensional shape, such as, but not limited to: triangular prism, square prism, hexagonal prism, cylinder, cone, partial sphere, partial ovoid, irregular solids, and the like. The receptacle is shaped to accommodate these replaceable thermal subsystems.

Embodiments of the dual modality system of the present invention will be used in the following manner to enhance the effect of treatment to an area of a user's body. For illustrative purposes, use of sixth embodiment dual modality system 500 will be presented.

In one embodiment, the user first activates replaceable thermal subsystem 580 and places subsystem 580 onto first surface 523 of durable energy subsystem chassis 520. Then user weaves, or laces end tabs 560 of belt 550 through slots 528 of durable energy subsystem chassis 520. In the next step, user removes any release paper covering regions having adhesive, and places dual modality system 500 on the desired treatment area of a user's body. So, areas of contact between dual modality system 500 and the treatment area are second surface 524 of durable energy subsystem chassis 520 and second surface 564 of tabs 560. The attachment has sufficient attachment strength to prevent separation dual modality system 500 from the treatment area during routine movements of the skin.

In some embodiments, dual modality system 500 is purchased as a pre-assembled device with replaceable thermal subsystems 580 attached to or formed on the first surface 523 of durable energy subsystem chassis 520. In these embodiments, dual modality system 500 may be viewed as a one-time use treatment device. User activates replaceable thermal subsystem 580 just prior to placing dual modality system 500 on the desired treatment area of the user's body. In these embodiments, there may be release liners disposed on any or all adhesives surfaces for protection prior to use.

In other embodiments, a user may purchase a kit containing durable energy subsystem chassis 520 and belt 550, along with one or more separately packed replaceable thermal subsystems 580. Kits may contain one or more durable energy subsystem chassis 520, as well as one or more, two or more, five or more, or ten or more, or twenty or more replaceable thermal subsystems 580. In these embodiments, replaceable thermal subsystems 580 may be packed in air-tight packs to prevent initiation of their thermal reaction. In these embodiments, durable energy subsystem chassis 520 and belt 550 are both reusable. For each use, user activates replaceable thermal subsystem 580 just prior to or after assembling dual modality system 500, and then places dual modality system 500 on the desired treatment area of the user's body. There may be release liners disposed on any or all surfaces to protect the surface(s) prior to use.

In still other embodiments, a user may purchase a kit containing durable energy subsystem chassis 520 with one or more separately packed replaceable thermal subsystems 580 and belts 550. Kits may contain one or more durable energy subsystem chassis 520, as well as one or more, two or more, five or more, or ten or more, or twenty or more replaceable thermal subsystems 580 and belts 550. In these embodiments, replaceable thermal subsystems 580 may be packed in air-tight packs to prevent initiation of their thermal reaction. In these embodiments, durable energy subsystem chassis 520 is reusable. For each use, user activates replaceable thermal subsystem 580 just prior to or after assembling dual modality system 500, and then places dual modality system 500 on the desired treatment area of the user's body. There may be release liners disposed on any or all surfaces to protect the surface(s) prior to use.

In yet other embodiments, kits may contain one or more pre-assembled dual modality system 500, with one or more additional separately packed replaceable thermal subsystems 580 and belts 550. Kits may contain one or more, two or more, five or more, or ten or more, or twenty or more replaceable thermal subsystems 580 and belts 550. In these embodiments, replaceable thermal subsystems 580 may be packed in air-tight packs to prevent initiation of their thermal reaction. In these embodiments, durable energy subsystem chassis 520, and sometimes belts 550, are reusable. For each use, user activates replaceable thermal subsystem 580 just prior to placing dual modality system 500 on the desired treatment area of the user's body. There may be release liners disposed on any or all surfaces to protect the surface(s) prior to use.

Once dual modality system 500 has been placed on the desired treatment area of the user's body, user initiates the durable energy subsystem chassis 520 treatment cycle, energizing the energy emitters 570. This can be accomplished, for example, by the user pressing and on/off switch located on durable energy subsystem chassis 520 or, if the dual modality system 500 includes at least one component arranged and configured to communicate data through wired or wireless communication with external devices, using a smart device such as a cell phone to initiate the treatment cycle. As mentioned previously, treatment cycles can use light, heat, cooling, vibration, or combinations thereof. The length of the treatment cycle will depend on the treatment being performed. In some embodiments, durable energy subsystem chassis 520 treatment cycle is less than sixty (60) minutes, or thirty (30) minutes, or ten (10) minutes, or five (5) minutes, or one (1) minute.

The treatment cycle is next completed. In some embodiments, the user manually completes the cycle by, for example, by the user pressing and on/off switch located on durable energy subsystem chassis 520, or using a smart device such as a cell phone to initiate the treatment cycle. In other embodiments, durable energy subsystem chassis 520 has a timing mechanism, and dual modality system 500 will shut down upon completion of the treatment cycle.

Next, dual modality system 500 has been is separated from the treatment area.

The durable energy subsystem chassis may be formed by any means known to those skilled in the art. Materials of construction include polymers and elastomers, including without limitation, thermoplastic elastomers ("TPE"), thermoplastic urethanes ("TPU"), silicones, acrylonitrile butadiene styrene polymers ("ABS"), among may flexible and more rigid materials. Preferably, the materials include sufficient transmissive properties to transmit the energy, e.g., light, electromagnetic field, microcurrent, electrical stimulation (TENS trans-cutaneous electrical nerve stimulation, MENS, PENS), iontophoresis, sonophoresis, and/or motion, e.g., ultrasound and/or vibration to the treatment surface. In addition, for embodiments in which the replaceable thermal subsystem is placed over the emission region of the chassis, good thermal conductivity characteristics are also highly desirable.

While the durable energy subsystem chassis may be printed, cast, injection molded and/or overmolded in a series of steps, the chassis may also be made by forming (e.g., by molding) an upper housing and a lower housing (independently or as a clam-shell construction), and placing a flexible or semi flexible circuit board between the two housings and adhesively attaching the housings and circuit board (including power source and controller) together. Other assembly processes may be used, including those known for use in wearable electronics and smart textiles. For example, it may be helpful to locally modify the flexibility of the substrate and/or housing to mechanically reinforce regions where brittle components are intended to be positioned.

In the embodiments discussed above, the replaceable thermal subsystems having a thermal source are arranged and configured to couple the replaceable thermal subsystem to the chassis comprising a durable energy subsystem in a configuration wherein the thermal source is substantially superposed over the emission region of the chassis. In other embodiments, the thermal source is partially superposed over the emission regions of the chassis.

The devices described herein deliver phototherapy and thermal therapy, allowing for relief from musculoskeletal pain and other ailments (including injury to bones, joints, muscles, tendons, ligaments, or nerves).

A method of ameliorating pain uses the steps of assembling any of the systems described above, activating the replaceable thermal subsystem, attaching the system to a desired treatment area of a user's body, and activating the durable energy subsystem; wherein the replaceable thermal subsystem delivers thermal energy to the desired treatment area at a predetermined temperature range for at least one (1) minute, or five (5) minutes, or ten (10) minutes, or thirty (30) minutes, or less than or greater than sixty (60) minutes. The durable energy subsystem delivers energy from the group consisting of non-visible light electromagnetic radiation, visible light radiation, electromagnetic field, microcurrent, electrical stimulation, iontophoresis, sonophoresis and combinations thereof independently of the thermal energy.

In some embodiments, the thermal energy is at or above human body temperature. In other embodiments, the thermal energy is below human body temperature. The thermal energy subsystem comprises a phase change material, or provides an exothermic chemical reaction.

The durable energy subsystem is arranged and configured to deliver energy continuously in some embodiments, and discontinuously in other embodiments. The durable energy subsystem can also deliver pulsed energy in a predetermined pattern in some embodiments. In some embodiments, the predetermined pattern comprises a plurality of pulse trains separated by varying intervals of no energy delivery from the durable energy subsystem. As used herein, a pulse train can be a single extended continuous pulse or can be a sequence of individual pulses in a predetermined pattern.

In some embodiments, the durable energy subsystem is arranged and configured to deliver light energy from the group consisting of visible light and infrared light. The light energy density is greater than about 5 Joules/cm$^2$, or greater than about 10 Joules/cm$^2$.

EXAMPLE

A flex PCB board and 2 rigid PCB boards were fabricated by Sunstone Circuits (Mulino, Oreg.) using PCB123® software. Thirty-two red and thirty-two IR LED's were attached to the flex board, and 2 NiMH batteries were mounted to the ends of the flex board. Rigid boards for the Bluetooth module and the charging module were fixed to the ends of the flex board.

The Flex-Rigid board assembly with LED's and batteries were then placed in a mold and cast with silicone and cured at room temperature for 24 hours. A second casting with silicone was performed after the first cure followed by another 24-hour cure at room temperature.

A disposable heat pack was created by taking a 55° C. heat pack (50-60° C. range) made from iron powder, carbon, vermiculite, and sodium chloride and thermally sealed in a PET/PE substrate. An adhesive laminate comprising a woven backing, acrylic adhesive, and protective facing tabs was laser cut to form an adhesive bandage that would be the vehicle to deliver therapy from the heat pack and to attach the light bandage to a user's body.

What is claimed is:

1. A method comprising the steps of:
    a) unwrapping a replaceable thermal subsystem arranged and configured to deliver thermal energy from packaging material;
    b) assembling a system comprising:
        i) a durable energy subsystem arranged and configured to deliver energy; and
        ii) the replaceable thermal subsystem arranged and configured to be coupled to the durable energy subsystem; and
    c) activating the replaceable thermal subsystem;
    d) attaching the system to a desired treatment area of a user's body; and
    e) activating the durable energy subsystem; wherein the replaceable thermal subsystem delivers thermal energy to the desired treatment area at a predetermined temperature range for at least 30 minutes, and the durable energy subsystem delivers energy from the group consisting of non-visible light electromagnetic radiation, visible light radiation, electromagnetic field, microcurrent, electrical stimulation, iontophoresis, sonophoresis and combinations thereof independently of the thermal energy.

2. The method of claim 1 wherein the thermal energy is at or above human body temperature.

3. The method of claim 1 wherein the thermal energy is below human body temperature.

4. The method of claim 1 wherein the thermal energy subsystem comprises a phase change material.

5. The method of claim 1 wherein the thermal energy subsystem provides an exothermic chemical reaction.

6. The method of claim 1 wherein the durable energy subsystem is arranged and configured to deliver energy continuously.

7. The method of claim 1 wherein the durable energy subsystem delivers energy discontinuously.

8. The method of claim 7 wherein the durable energy subsystem delivers pulsed energy in a predetermined pattern.

9. The method of claim 1 wherein the durable energy subsystem is arranged and configured to deliver light energy from the group consisting of visible light and infrared light.

10. The method of claim 9 wherein the light energy density is greater than about 5 Joules/cm$^2$.

11. The method of claim 10 wherein the light energy density is greater than about 10 Joules/cm$^2$.

12. The method of claim 1 wherein the durable energy subsystem communicates data with an external device.

13. The method of claim 1 wherein the steps of the method ameliorate pain.

14. The method of claim 1 further comprising the steps of:
    f) removing the system from the desired treatment area of a user's body;
    g) disassembling the system by removing a used replaceable thermal subsystem;
    h) unwrapping an unused replaceable thermal subsystem arranged and configured to deliver thermal energy from packaging material
    i) re-assembling the system by coupling the unused replaceable thermal subsystem to the durable energy subsystem; and
    j) repeating steps c)-e).

* * * * *